(12) United States Patent
Akitomi

(10) Patent No.: US 9,311,447 B2
(45) Date of Patent: *Apr. 12, 2016

(54) METHOD FOR IDENTIFYING NUCLEOTIDE SEQUENCE, METHOD FOR ACQUIRING SECONDARY STRUCTURE OF NUCLEIC ACID MOLECULE, APPARATUS FOR IDENTIFYING NUCLEOTIDE SEQUENCE, APPARATUS FOR ACQUIRING SECONDARY STRUCTURE OF NUCLEIC ACID MOLECULE, PROGRAM FOR IDENTIFYING NUCLEOTIDE SEQUENCE, AND PROGRAM FOR ACQUIRING SECONDARY STRUCTURE OF NUCLEIC ACID MOLECULE

(75) Inventor: Jou Akitomi, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 738 days.

This patent is subject to a terminal disclaimer.

(21) Appl. No.: 13/477,714

(22) Filed: May 22, 2012

(65) Prior Publication Data

US 2013/0158884 A1    Jun. 20, 2013

Related U.S. Application Data

(63) Continuation of application No. 12/446,199, filed as application No. PCT/JP2007/070366 on Oct. 18, 2007, now Pat. No. 8,200,441.

(30) Foreign Application Priority Data

Oct. 18, 2006   (JP) .................................. 2006-283757

(51) Int. Cl.
*G06F 19/22*    (2011.01)
*G06F 19/16*    (2011.01)

(52) U.S. Cl.
CPC ................ *G06F 19/22* (2013.01); *G06F 19/16* (2013.01)

(58) Field of Classification Search
None
See application file for complete search history.

(56) References Cited

U.S. PATENT DOCUMENTS 8,200,441 B2 *   6/2012  Akitomi .......................... 702/27
2004/0121398 A1  6/2004  Doi et al.

FOREIGN PATENT DOCUMENTS

| JP | 05-507413 A | 10/1993 |
|---|---|---|
| JP | 2000-060553 A | 2/2000 |
| JP | 2005-245254 A | 9/2005 |
| JP | 2005-284595 A | 10/2005 |
| JP | 2008-102675 A | 5/2008 |
| WO | 01/67299 A1 | 9/2001 |
| WO | 2006/004182 A1 | 1/2006 |

OTHER PUBLICATIONS

Harukazu Suzuki, et al., Genome Network, Kyoritsu Shuppan Co., Ltd., Dec. 15, 2004, pp. 2673-2677, vol. 49, No. 17.
Joe Akitomi, et al., "Secondary structure prediction algorithm for RNA aptamers," Dai 8 Kai RNA Meeting, Jul. 18, 2006, p. 64.
Yoshikazu Nakamura, et al., "Biotechnology Series: Frontier of RNA Engineering," CMC Publishing Co., Ltd., pp. 139-141.
Laserson, U. et. al.: "Predicting candidate genomic sequences that correspond to synthetic functional RNA motifs", Nucleic acids research, 2005, vol. 33, No. 18, p. 6057-6069.
Ouchi, Idenshi Igaku Mook 4 (Gene Medicine Mook 4), 2006.
Hirao, I., et. al.: "RNA Aptamers That Bind to and Inhibit the Ribosome-inactivating Protein, Pepocin", The Journal of biological chemistry, vol. 275, No. 7, Issue of Feb. 18, 2000; pp. 4943-4948.
Liu, et al., "Screening of functional antidotes of RNA aptamers against bovine thrombin", FEBS Letters, Elsevier B.V., Amsterdam, NL, vol. 562, No. 1-3, Mar. 26, 2004, pp. 125-128, XP004829567, ISSN: 0014-5793.
Liu, et al., "RNA aptamers specific for bovine thrombin", Journal of Molecular Recognition, Heyden & Son Ltd., London, GB, vol. 16, No. 1, Jan. 1, 2003, pp. 23-27, XP002479553, ISSN: 0952-3499.
Kwon, et al., "The SL1 stem-loop structure at the 5'-end of potato virus X RNA is required for efficient binding to host proteins and for viral infectivity.", Molecules and Cells, Feb. 28, 2006, LNKDPUBMED: 16511348, vol. 21, No. 1, Feb. 28, 2006, pp. 63-75, XP002614879, ISSN: 1016-8478.
Wang, et al., "RNA molecules that specifically and stoichiometrically bind aminoglycoside antibiotics with high affinities", Biochemistry, American Chemical Society, US, vol. 35, Jan. 1, 1996, pp. 12338-12346, XP002155142, ISSN: 0006-2960.
Ulrich, et al., "Vitro Selection of RNA Aptamers That Bind to Cell Adhesion Receptors of Trypanosoma cruzi and Inhibit Cell Invasion", Journal of Biological Chemistry, 2002, pp. 20756-20762, vol. 277.

* cited by examiner

*Primary Examiner* — John S Brusca
(74) *Attorney, Agent, or Firm* — Sughrue Mion, PLLC

(57) ABSTRACT

The object of the present invention is to provide a method for identifying a nucleotide sequence necessary for expressing affinity for a target substance with respect to a nucleotide sequence of a nucleic acid molecule such as an aptamer having such affinity for the target substance, based on similarity between nucleotide sequences and an evaluated value of the affinity of the nucleotide sequence, and a method for predicting a secondary structure of the nucleic acid molecule including the identified nucleotide sequence. The method of present invention includes the steps of extracting a single-stranded region by excluding based capable of forming a stem structure from the nucleotide sequence of the nucleic acid molecule; and searching a motif sequence from the single-stranded region, based on an evaluated value of the affinity.

24 Claims, 13 Drawing Sheets

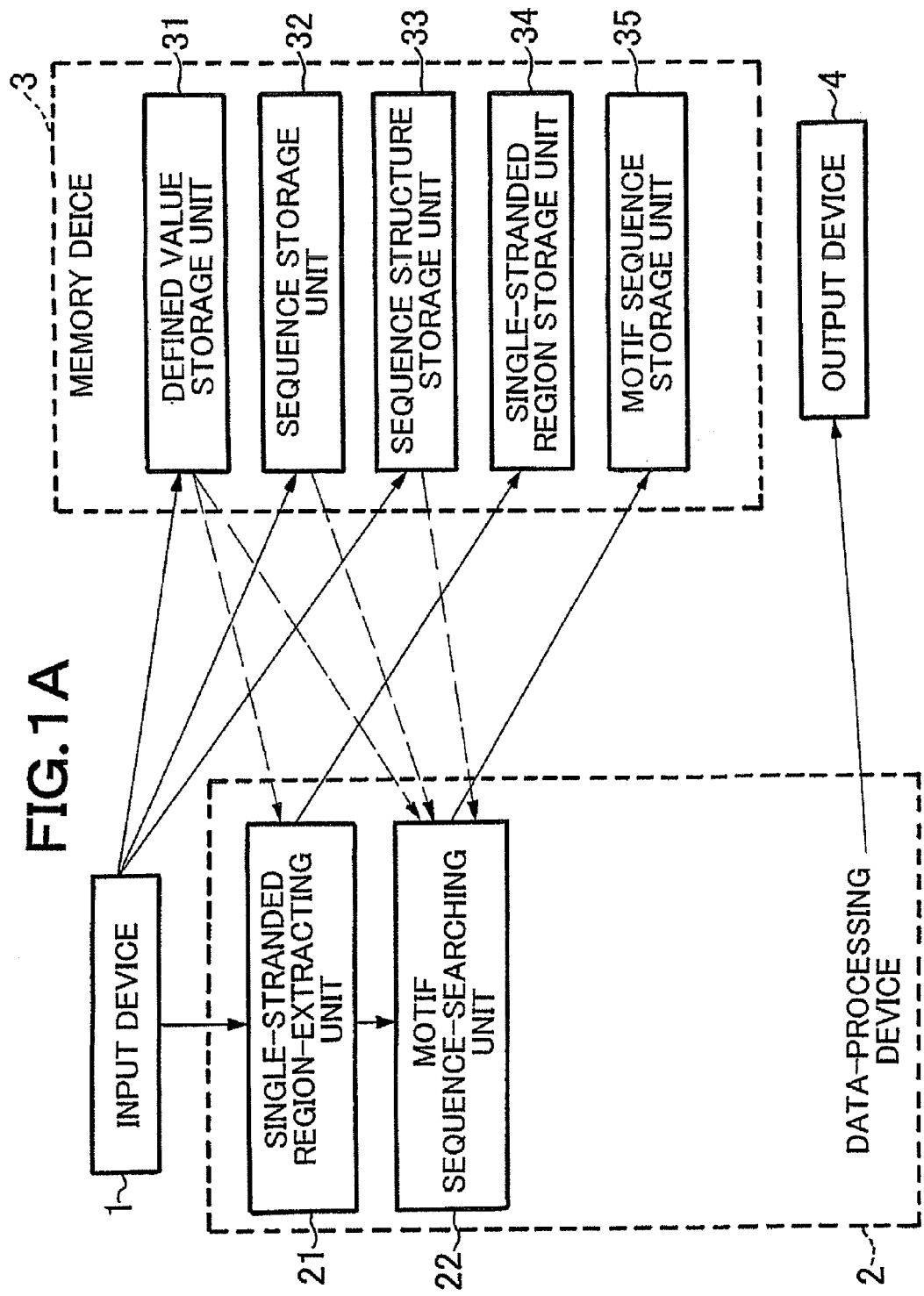

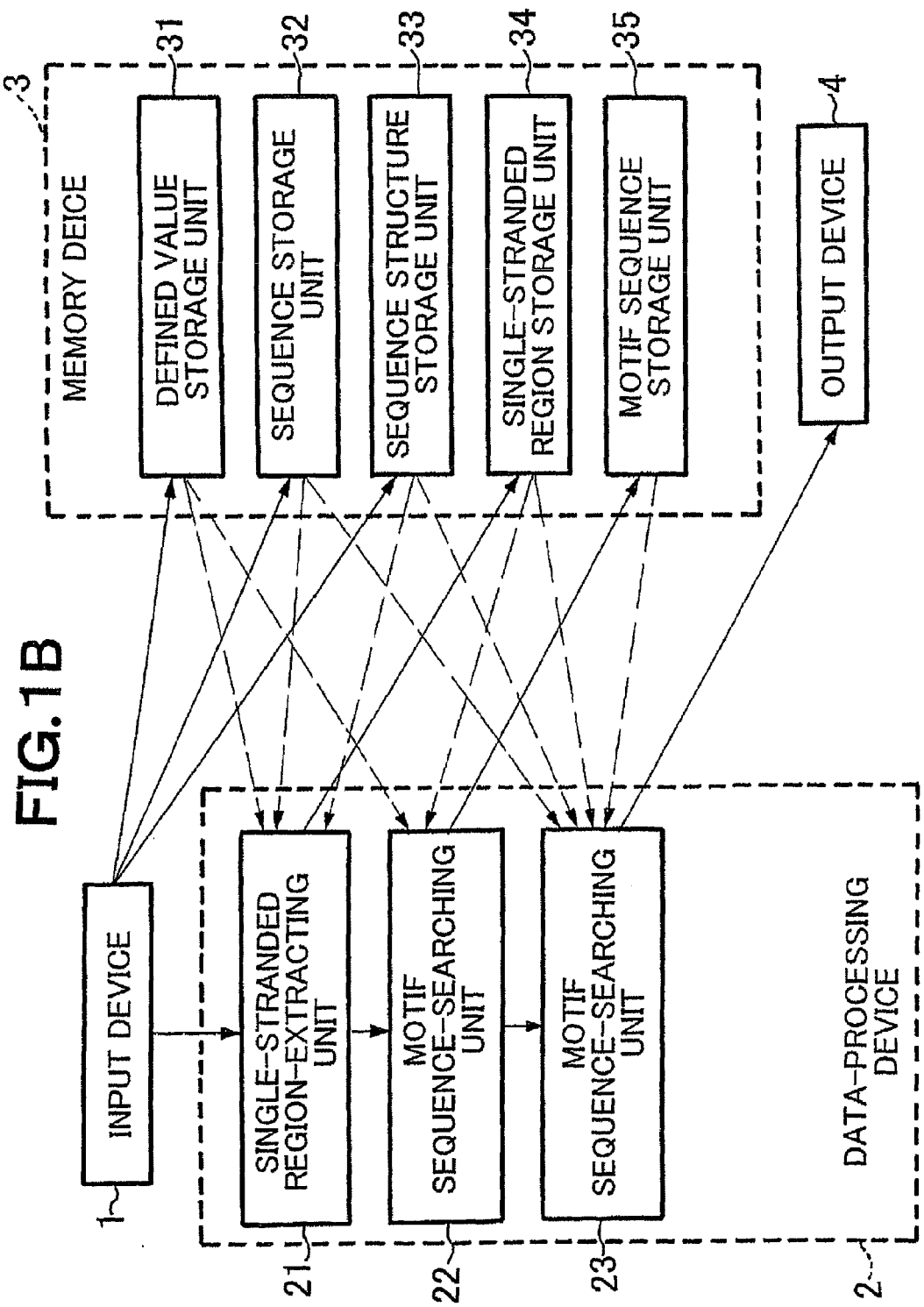

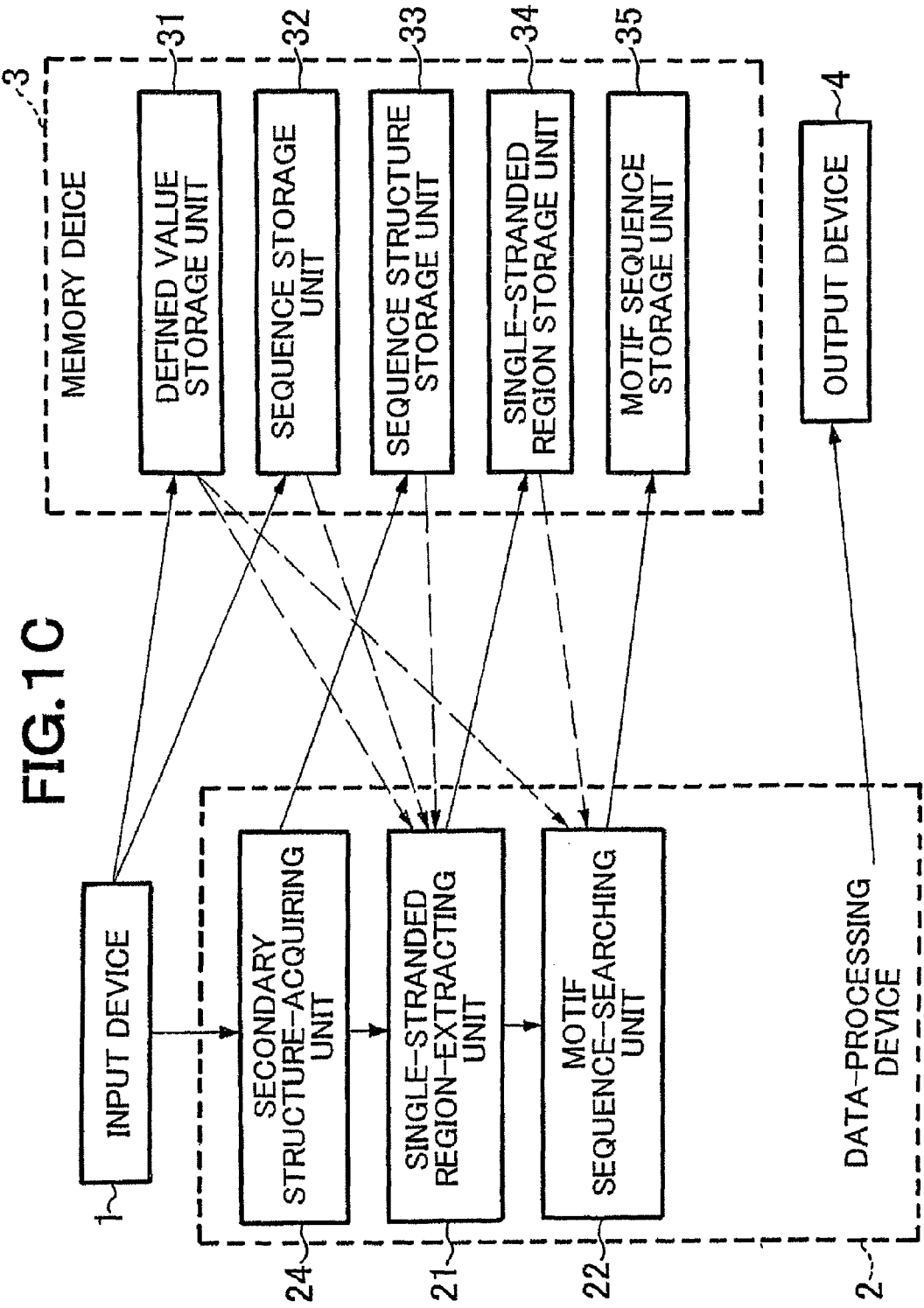

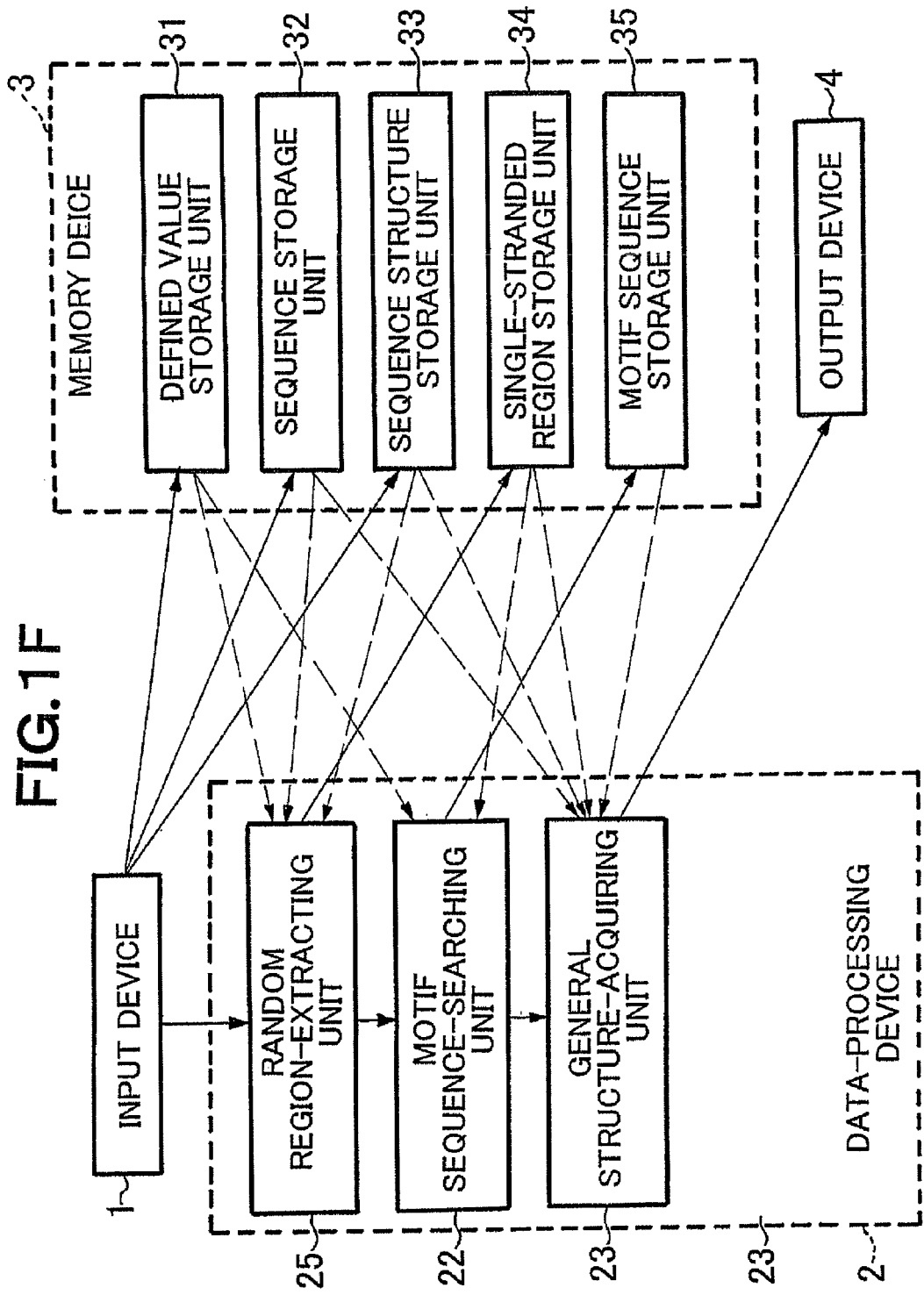

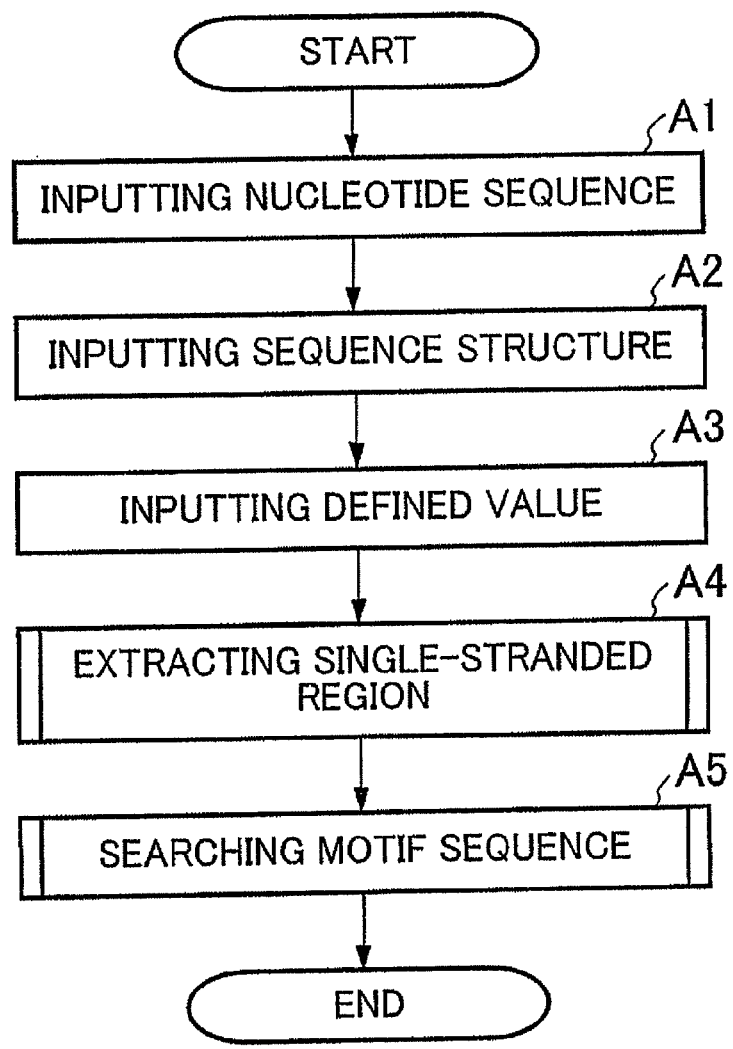

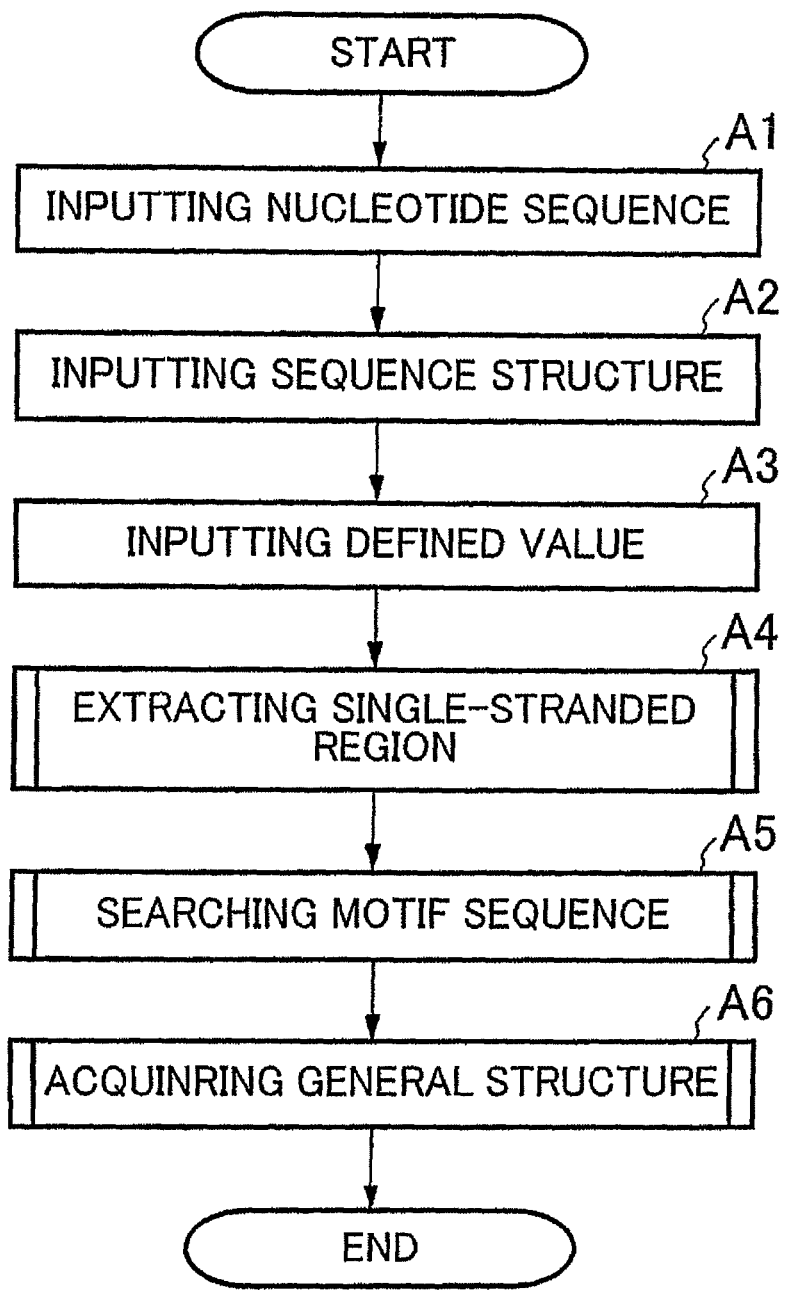

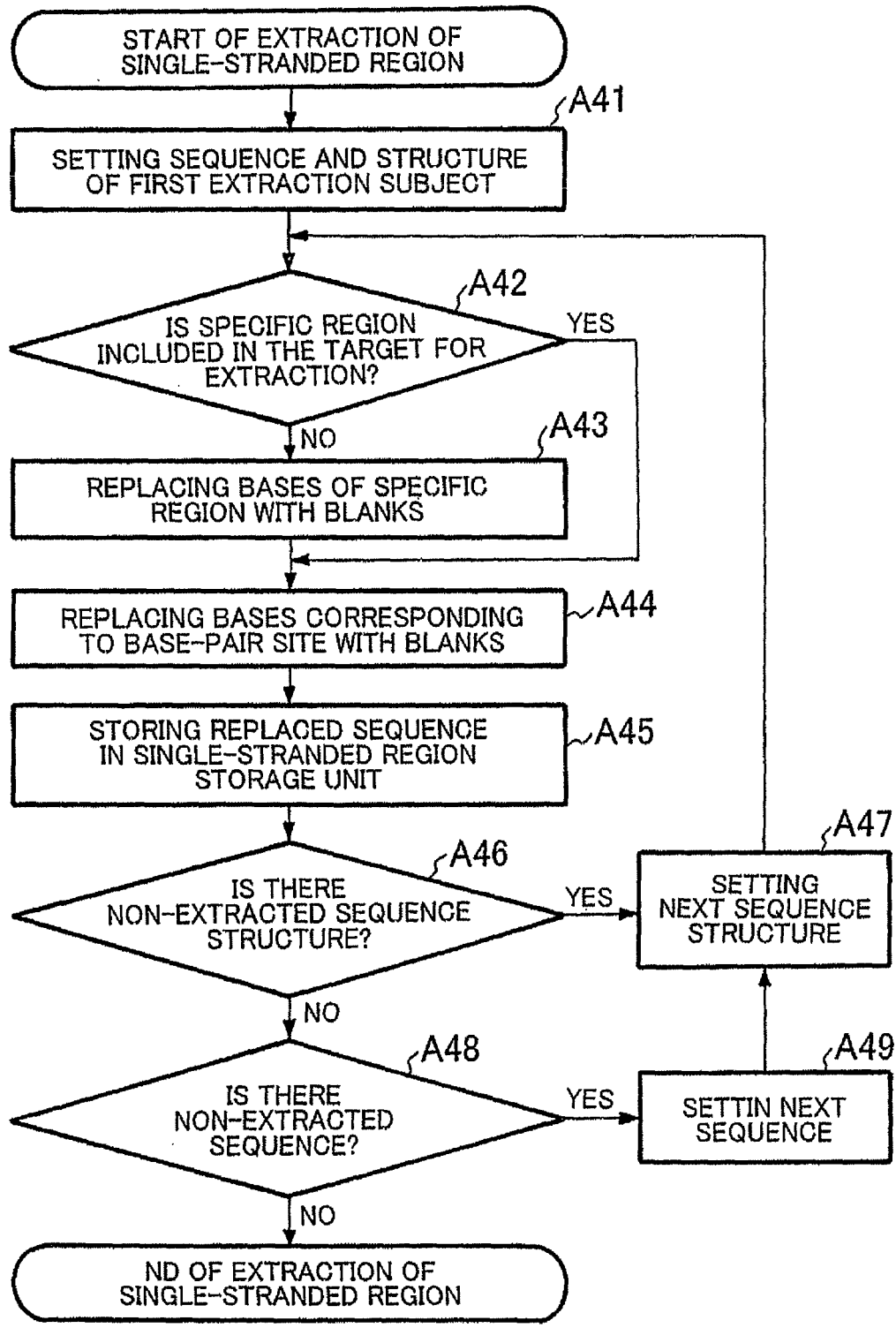

FIG.7

```
SEQUENCE 1      AAAA   CGCGAAAACGCG   AAUU
STRUCTURE1-1    ::((   ((((::::))))   ::))
STRUCTURE1-2    ((::   ((((::::))))   ::))

SEQUENCE 2      AAAA   GCGCAGAAGCGC   AAUU
STRUCTURE2-1    ::((   ((((::::))))   ::))
STRUCTURE2-2    ((::   ((((::::))))   ::))

PRIMER                PRIMER
                REGION                REGION
```

FIG.8

```
SINGLE-STRANDED REGION 1-1  ----AAAA----
SINGLE-STRANDED REGION 1-2  ----AAAA----

SINGLE-STRANDED REGION 2-1  ----AGAA----
SINGLE-STRANDED REGION 2-2  ----AGAA----
```

AAAA    CGCGAAAACGCG    AAUU         CGCGAAAACGCG
: :((   ((((: : : :))))  : :))       ((((: : : :))))

METHOD FOR IDENTIFYING NUCLEOTIDE SEQUENCE, METHOD FOR ACQUIRING SECONDARY STRUCTURE OF NUCLEIC ACID MOLECULE, APPARATUS FOR IDENTIFYING NUCLEOTIDE SEQUENCE, APPARATUS FOR ACQUIRING SECONDARY STRUCTURE OF NUCLEIC ACID MOLECULE, PROGRAM FOR IDENTIFYING NUCLEOTIDE SEQUENCE, AND PROGRAM FOR ACQUIRING SECONDARY STRUCTURE OF NUCLEIC ACID MOLECULE

CROSS REFERENCE TO RELATED APPLICATIONS

This application is a continuation of U.S. patent application Ser. No. 12/466,199, filed on Apr. 17, 2009, which is a National Stage of International Application No. PCT/JP2007/070366, filed on Oct. 18, 2007, which claims priority from Japanese Patent Application No. 2006-283757, filed on Oct. 18, 2006, the contents of all of which are incorporated herein by reference in their entirety.

TECHNICAL FIELD

The present invention relates to a method for identifying a nucleotide sequence, a method for acquiring a secondary structure of a nucleic acid molecule, and an apparatus and program for executing these methods.

BACKGROUND ART

It has been well-known that nucleic acid molecules such as DNA and RNA have a function of producing proteins through transcription/translation. However, a large number of molecular species (such as ribozymes and RNAi) having a function due to interaction with proteins and high-molecular-weight substances (i.e. a function that is different from the originally observed function of nucleic acid molecules) have been discovered, and their application to the therapeutic field, etc. attracts attention. In particular, aptamers attract attention as molecular species which exhibit their function by binding directly to target substances such as proteins, high-molecular-weight materials, pharmaceuticals, etc. At present, a SELEX (Systematic Evolution of Ligands by EXponential enrichment) method is known as a general method of obtaining aptamers (see Patent Document 1). The aptamers and the SELEX method are described in detail in Non-Patent document 1.

One feature of aptamers obtained by the SELEX method is that aptamers are composed of an arbitrary primer sequence and a random sequence of arbitrary length. Another feature of aptamers obtained by SELEX method is that, even if promising candidates of aptamers are screened sufficient number of times in the SELEX method, there are plural types of finally-obtained aptamers.

It has been known that aptamers having such features includes many redundant regions such as a primer sequence and that the region necessary for the aptamer to actually bind to the target substance is a part of bases constituting the aptamer. Therefore, identification of the region necessary for the aptamer to bind to the target substance is very important not only in improving the efficiency of production of aptamers but also in understanding the mode of binding of the aptamer to the target substance.

However, in order to identify the region necessary for the aptamer to bind to the target substance, it has been conventionally required to conduct a binding experiment in vitro or the like using an obtained aptamer and its target substance. For example, redundant sequences that are considered unnecessary for the obtained aptamers to bind to their target substances are removed from the aptamers by way of digestion according to a genetic engineering technique so as to prepare a series of nucleotide sequences, and it is required to conduct a binding experiment or the like using the nucleotide sequences and the target substances in order to identify region necessary for binding. Such a method involves not only a large amount of labor, and after all requires trial and error based on experimenter's experience (for example, how much obtained aptamers need to be digested). Therefore, a method for efficiently identifying a region of the aptamer which is essential for binding to the target substance has been sought.

Patent Document 1: Published Japanese Translation No. H05-507413 of the PCT International Publication.

Non-Patent Document 1: "Biotechnology Series: Frontier of RNA Engineering" edited by Yoshikazu Nakamura and Shoji Ochi, CMC Publishing Co., Ltd, pp. 139-141.

DISCLOSURE OF THE INVENTION

Problems to be Solved by the Invention

The present invention was achieved in view of the problem described above. The object of the present invention is to provide a method for identifying a nucleotide sequence necessary for expressing affinity for a target substance with respect to a nucleotide sequence of a nucleic acid molecule such as an aptamer having the affinity for the target substance, based on similarity between nucleotide sequences and an evaluated value of the affinity of the nucleotide sequence, and a method for predicting a secondary structure of a nucleic acid molecule including the identified nucleotide sequence. Another object of the present invention is to provide an apparatus for identifying a nucleotide sequence and an apparatus for acquiring a secondary structure of a nucleic acid molecule. Still another object of the present invention is to provide a program for identifying a nucleotide sequence and a program for acquiring a secondary structure of a nucleic acid molecule, which executes these methods.

Means for Solving the Problems

The method for identifying a nucleotide sequence according to the present invention is a method for identifying a nucleotide sequence necessary for expressing affinity for a target substance with respect to a nucleotide sequence of a nucleic acid molecule having the affinity, the method, including the steps of: extracting a single-stranded region by excluding bases capable of forming a stem structure from the nucleotide sequence of the nucleic acid molecule; and searching a motif sequence from the single-stranded region, based on an evaluated value of the affinity.

The method for acquiring a secondary structure of a nucleic acid molecule according to the present invention is a method for acquiring a secondary structure of a nucleic acid molecule including a nucleotide sequence necessary for expressing affinity for a target substance with respect to a nucleotide sequence of a nucleic acid molecule having the affinity, the method, including the steps of: extracting a single-stranded region by excluding bases capable of forming a stem structure from the nucleotide sequence of the nucleic acid molecule; searching a motif sequence from the single-stranded region, based on an evaluated value of the affinity; and acquiring a general structure from a secondary structure of the nucleic acid molecule, based on the single-stranded region that accords with the motif sequence and based on bases forming the stem structure positioned at both ends of the single-stranded region.

The apparatus for identifying a nucleotide sequence according to the present invention is an apparatus for identifying a nucleotide sequence necessary for expressing affinity for a target substance with respect to a nucleotide sequence of a nucleic acid molecule having the affinity, the apparatus, including: a single-stranded region-extracting unit that extracts a single-stranded region by excluding bases capable of forming a stem structure from the nucleotide sequence of the nucleic acid molecule; and a motif sequence-searching unit that searches a motif sequence from the single-stranded region, based on an evaluated value of the affinity.

The apparatus for acquiring a secondary structure of a nucleic acid molecule according to the present invention is an apparatus for acquiring a secondary structure of a nucleic acid molecule including a nucleotide sequence necessary for expressing affinity for a target substance with respect to a nucleotide sequence of a nucleic acid molecule having the affinity, the apparatus, including: a single-stranded region-extracting unit that extracts a single-stranded region by excluding bases capable of forming a stem structure from the nucleotide sequence of the nucleic acid molecule; a motif sequence-searching unit that searches a motif sequence from the single-stranded region, based on an evaluated value of the affinity; and a general structure-acquiring unit that acquires a general structure from a secondary structure of the nucleic acid molecule, based on the single-stranded region that accords with the motif sequence and based on bases forming the stem structure positioned at both ends of the single-stranded region.

The program for identifying a nucleotide sequence according to the present invention is a program for identifying a nucleotide sequence necessary for expressing affinity for a target substance with respect to a nucleotide sequence of a nucleic acid molecule having the affinity, the program, executing the steps of: extracting a single-stranded region by excluding bases capable of forming a stem structure from the nucleotide sequence of the nucleic acid molecule; and searching a motif sequence from the single-stranded region, based on an evaluated value of the affinity.

The program for obtaining a secondary structure of a nucleic acid molecule according to the present invention is a program for acquiring a secondary structure of a nucleic acid molecule including a nucleotide sequence necessary for expressing affinity for a target substance with respect to a nucleotide sequence of a nucleic acid molecule having the affinity, the program, executing the steps of: extracting a single-stranded region by excluding bases capable of forming a stem structure from the nucleotide sequence of the nucleic acid molecule; searching a motif sequence from the single-stranded region, based on an evaluated value of the affinity; and acquiring a general structure from a secondary structure of the nucleic acid molecule, based on the single-stranded region that accords with the motif sequence and based on bases forming the stem structure positioned at both ends of the single-stranded region.

In the present invention, the apparatus for identifying a nucleotide sequence and the program for identifying a nucleotide sequence refer respectively to an apparatus and a program that execute the method for identifying a nucleotide sequence according to the present invention; the apparatus for acquiring a secondary structure of a nucleic acid molecule and the program for acquiring a secondary structure of a nucleic acid molecule refer respectively to an apparatus and a program that execute the method for acquiring a secondary structure of a nucleic acid molecule according to the present invention. In the present invention, the "nucleic acid molecule" refers to various genes such as DNA and RNA.

Effect of the Invention

According to the first effect of the present invention, an important structure of a nucleic acid molecule such as an aptamer can be extracted without performing an experiment. As a result, information important for obtaining a highly practical nucleic acid molecule from which redundant sites that have no relevance to the function of molecule were eliminated can be efficiently obtained.

This is because a sequence (motif sequence) preserved commonly in a very limited region that is included in a single-stranded region when forming a second structure; and the minimum secondary structure including a loop site including this sequence are extracted by computational simulation from a random site of aptamers obtained by the SELEX method.

According to the second effect of the present invention, a secondary structure of a nucleic acid molecule such as an aptamer can be predicted with high accuracy.

This is because a plurality of candidates for the secondary structure incorporated as input information is narrowed by selecting those having a motif sequence in a loop site, thereby stringently selecting candidates for the structure.

According to the third effect of the present invention, a motif sequence having an important function for a nucleic acid molecule such as an aptamer to bind to its target substance can be extracted.

This is because, in the stage of selecting candidates for the motif sequence, the candidates for the motif sequence are evaluated by a score weighted with an evaluated value of binding affinity between a nucleic acid molecule such as an aptamer and its target substance, whereby a motif sequence having an important function for the nucleic acid molecule to bind to its target substance can be extracted more easily, compared with simple evaluation by appearance-frequency counting.

BRIEF DESCRIPTION OF THE DRAWINGS

FIG. 1A is a schematic diagram of the apparatus for identifying a nucleotide sequence according to the present invention.

FIG. 1B is a schematic diagram of the apparatus for acquiring a secondary structure of a nucleic acid molecule according to the present invention.

FIG. 1C is a schematic diagram showing an example of the apparatus for identifying a nucleotide sequence according to the present invention that includes a secondary structure-predicting unit.

FIG. 1F is a schematic diagram showing an example of the apparatus for acquiring a secondary structure of a nucleic acid molecule according to the present invention that includes a random region-extracting unit.

FIG. 2 shows an example of a nucleotide sequence having base pairs and a single-stranded region.

FIG. 3A is a flowchart showing an outline of the method of identifying a nucleotide sequence according to the present invention.

FIG. 3B is a flowchart showing an outline of the method for acquiring a secondary structure of a nucleic acid molecule according to the present invention.

FIG. 4 is a flowchart showing an outline of extraction of a single-stranded region.

FIG. 7 shows an example of nucleic acid molecules SEQUENCE 1 (SEQ ID NO: 1) and SEQUENCE 2 (SEQ ID NO: 2), and their structures.

FIG. 8 shows an example of a single-stranded region with respect to Sequence 1 or 2 shown in FIG. 7.

DESCRIPTION OF SYMBOLS

Figure 1D:
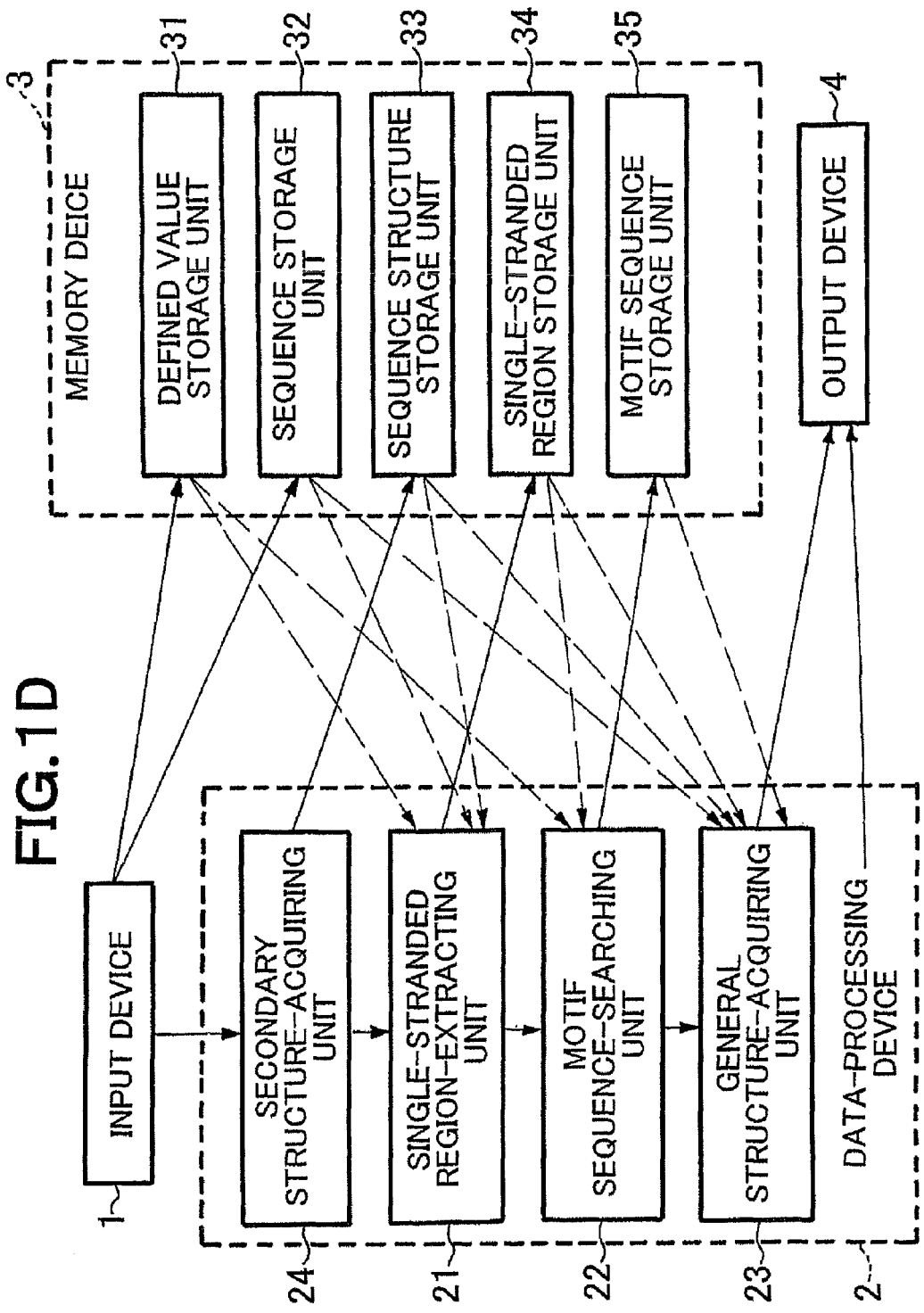
FIG. 1D is a schematic diagram showing an example of the apparatus for acquiring a secondary structure of a nucleic acid molecule according to the present invention that includes a secondary structure-predicting unit.

The reference numeral "1" refers to an input device; the reference numeral "2" refers to a data-processing device; the reference numeral "3" refers to a storage device; the reference numeral "4" refers to an output device; the reference numeral "21" refers to a single-stranded region-extracting unit; the reference numeral "22" refers to a motif sequence-searching unit; the reference numeral "23" refers to a general structure-acquiring unit; the reference numeral "24" refers to a secondary structure-predicting unit; the reference numeral "25" refers to a random region-extracting unit; the reference numeral "31" refers to a defined value storage unit; the reference numeral "32" refers to a sequence storage unit; the reference numeral "33" refers to a sequence structure storage unit; the reference numeral "34" refers to a single-stranded region storage unit; and the reference numeral "35" refers to a motif sequence storage unit.

BEST MODE FOR CARRYING OUT THE INVENTION

Hereinafter, preferable embodiments of the present invention will be described with reference to the drawings.
<The Method for Identifying a Nucleotide Sequence, the Apparatus for Identifying a Nucleotide Sequence and the Program for Identifying a Nucleotide Sequence According to the Present Invention>
(Configuration of the Apparatus for Identifying a Nucleotide Sequence According to the Present Invention, Function of Each Component, Etc.)

With reference to FIG. 1A, the configuration of the apparatus for identifying a nucleotide sequence according to the present invention is described. FIG. 1A is a schematic diagram of the apparatus for identifying a nucleotide sequence according to the present invention. The apparatus for identifying a nucleotide sequence according to the present invention includes an input device 1 such as a keyboard, a data-processing device 2 that actuates by program control, a storage device 3 that stores information, and an output device 4 such as a display or printer.

The data-processing device 2 includes a single-stranded region-extracting unit 21 and a motif sequence-searching unit 22.

The single-stranded region-extracting unit 21 extracts a single-stranded region by excluding bases capable of forming a stem structure from the nucleotide sequence of a nucleic acid molecule inputted through the input device 1. For example, the single-stranded region-extracting unit 21 retrieves information of each sequence from the sequence storage unit 32, and retrieves a sequence structure (such as in results of secondary structure prediction) with respect to each nucleotide sequence from the sequence structure storage unit 33. Then, based on such information, the single-stranded region-extracting unit 21 replaces, with blanks, bases capable of forming a complementary base pair (stem structure) such as A and U or G and C in the secondary structure of each sequence, thereby extracting a candidate for a single-stranded region of the nucleotide sequence. The results are extracted with respect to the sequence structure of each sequence, and are stored in the single-stranded region storage unit 34. In addition, the single-stranded region-extracting unit 21 may replace, by blanks, bases constituting a primer region included in a nucleotide sequence of a nucleic acid molecule such as an aptamer in the same manner as in the above-mentioned stem structure. In this case, the single-stranded region-extracting unit 21 may acquire, from the defined value storage unit 31, information as to whether or not the bases constituting a primer sequence are assessed as the above-mentioned excluded bases. Such acquisition of the information can prevent only primer sequences from being assessed as motif sequences in each of steps described below, whereby a nucleotide sequence necessary for binding to a target substance or the like included in a nucleic acid molecule can be obtained more efficiently and substantially.

The motif sequence-searching unit 22 searches a motif sequence from a single-stranded region extracted in the single-stranded region-extracting unit 21, based on an evaluated value (inputted through the input device 1) of the affinity of the nucleic acid molecule for its target substance. That is, the motif sequence-searching unit 22 retrieves the evaluated value of the affinity for the target substance of the nucleic acid molecule stored in the defined value storage unit 31, retrieves information of a single-stranded region of each sequence from the single-stranded region storage unit 34, and searches a motif sequence of each sequence based on the retrieved evaluated value and information. The motif sequence searched herein is a sequence pattern obtained by taking into consideration that appearance frequency of a specific sequence in a searched scope (appearance frequency which is determined by an arbitrary length inputted through the input device 1 and the number of arbitrary mismatches; and evaluated values (binding constant etc.) of the affinity, derived from the sequence, between the nucleic acid molecule and the target substance. Accordingly, the searched motif sequence is a sequence obtained by weighting the appearance frequency of the specific sequence with the evaluated value of the specific sequence. From the foregoing, a sequence pattern appearing in an aptamer which binds with higher binding affinity to a target substance may be defined preferentially as a motif sequence. If a plurality of sequence patterns is assessed as candidates for the motif sequence having the same score, then, a plurality of motif sequences may be present.

The motif sequence-searching unit 22 may have, in addition to the function of searching the motif sequence, a function of outputting the data to the output device 4 and a function of storing searching results in the motif sequence storage unit 35.

The storage device 3 includes a defined value storage unit 31, a sequence storage unit 32, a sequence structure storage unit 33 and a single-stranded region storage unit 34. The storage device 3 may include a motif sequence storage unit 35 in addition to these units.

The defined value storage unit 31 stores information such as the length of a motif sequence to be searched, the number of mismatches negligible in the sequence, information as to whether or not a specific region such as a primer sequence is included in the target for extraction of a single-stranded region or for searching of the motif sequence, a maximum score used for searching candidates for the motif sequence, and defined values such as evaluated values (inputted through the input device 1) indicating the affinity of nucleic acid molecules for the target substances. In particular, when these values are inputted through the input device 1, these inputted values may be updated with the corresponding defined values, thereby storing the updated values. The evaluated values indicating the affinity of nucleic acid molecules for the target substances are not particularly limited as long as the evaluated values are typical values indicating the degree of molecular-biological binding of nucleic acid molecules to target substances. For example, a binding constant (Kd) obtained by examination of binding of a radio-labeled nucleic acid molecule to its target substance in a test tube or by examination with "BIACORE 2000" based on the principle of SPR (surface plasmon resonance) analysis. As an example of the specific region, a primer sequence can be mentioned when the nucleic acid molecule is an aptamer obtained by the SELEX method. However, the specific region may be selected appropriately depending on the characteristics of the sequence of the nucleic acid molecule.

The sequence storage unit 32 stores nucleotide sequences of nucleic acid molecules such as DNA and RNA that are inputted through the input device 1. When RNA is to be inputted, the nucleotide sequence of the nucleic acid molecule may be an aptamer obtained by the SELEX method.

The sequence structure storage unit 33 stores results of prediction of one or more secondary structures with respect to the nucleotide sequence of each nucleic acid molecule inputted through the input device 1, as candidates for the sequence structure of the nucleotide sequence. The form of secondary structure of the nucleic acid molecule that is stored in the sequence structure storage unit 33 is not particularly limited. For example, base pairs (stem structure) that can be formed in the nucleic acid molecule inputted through the input device 1 may be expressed as "(" or ")" corresponding to bases forming the stem structure while a single-stranded region such as a loop may be expressed as ":" or the like. Based on such expression form, the nucleotide sequence shown in FIG. 2 can be expressed as "(((::::)))".

The single-stranded region storage unit 34 stores information of the sequence of the single-stranded region obtained by extraction with the single-stranded region-extracting unit 21.

The motif sequence storage unit 35 stores the motif sequence obtained by searching with the motif sequence-searching unit 22. The motif sequence is expressed by 5 letters, that is, four bases of A, C, G and U (T), and symbol "." indicating a mismatch.

(Steps in the Method for Identifying a Nucleotide Sequence and the Program for Identifying a Nucleotide Sequence According to the Present Invention, Actuation of the Apparatus for identifying a nucleotide sequence according to the present invention, etc.)

Hereinafter, with reference to FIG. 1A, FIG. 3A, FIG. 4 and FIG. 5, the steps in the method for identifying a nucleotide sequence and the program for identifying a nucleotide sequence according to the present invention, actuation of the apparatus for identifying a nucleotide sequence, and behavior of the program for identifying a nucleotide sequence according to the present invention will be described in detail.

The nucleotide sequence of a nucleic acid molecule such as an aptamer obtained in the same SELEX method is inputted through the input device 1 as a target for identification (A1). A list of secondary structures of the nucleotide sequence of this nucleic acid molecule is inputted through the input device 1 (A2). If necessary, defined values such as an evaluated value (e.g. a binding constant) such as the affinity of the nucleic acid molecule for the target substance, the length of the nucleotide sequence that is subjected to searching of the motif sequence as described below, and the number of mismatches negligible in the motif sequence are inputted through the input device 1 (A3). The inputted nucleotide sequence of the nucleic acid molecule, the list of secondary structures, and the defined values are stored in the sequence storage unit 32, the sequence structure storage unit 33 and the defined value storage unit 31, respectively (A1, A2, A3).

Then, the single-stranded region-extracting unit 21 is used to extract a single-stranded region from the nucleotide sequence of the inputted nucleic acid molecule (A4). Extraction of the single-stranded region is described with reference to FIG. 4.

FIG. 4 is a flowchart showing an outline of extraction of a single-stranded region. The single-stranded region-extracting unit 21 retrieves, from the defined value storage unit 31, a value as to whether or not a specific region such as a primer sequence in the nucleotide sequence of the nucleic acid molecule is included in the region from which single-stranded regions are to be extracted. The single-stranded region-extracting unit 21 retrieves information of the nucleotide sequence of the nucleic acid molecule from the sequence storage unit 32, and simultaneously retrieves information of possible secondary structures (sequence structures) formed by each nucleic acid molecule from the sequence structure storage unit 33. Then, among the inputted nucleotide sequences of nucleic acid molecules, the single-stranded region-extracting unit 21 sets one nucleotide sequence as the first target for extraction and its corresponding sequence structure (A41). After setting, the single-stranded region-extracting unit 21 determines whether or not a specific region such as a primer sequence is included in the target for extraction (A42). If the specific region is not included in the target for extraction, the single-stranded region-extracting unit 21 replaces, by blanks, bases corresponding to the specific region in the set nucleotide sequence (A43). If the specific region is included in the target for extraction, the operation proceeds to the next step (A44) without executing Step A43. Then, the single-stranded region-extracting unit 21 references a sequence structure corresponding to the inputted nucleotide sequence of the nucleic acid molecule, and replaces, by blanks, bases forming a stem structure in the sequence structure (A44). When the step A44 is completed, the set nucleotide sequence is in the form of a sequence in which bases other than bases constituting a single-stranded region in the sequence are replaced by blanks, and therefore, the single-stranded region-extracting unit 21 allows information of the bases not replaced by blanks (i.e. the bases constituting a single-stranded region) to be stored in the single-stranded region storage unit 34 (A45). Then, the single-stranded region-extracting unit 21 determines whether or not a non-extracted sequence structure corresponding to the sequence is present with respect to the set nucleotide sequence (A46). If a non-extracted sequence structure is present (corresponding to "yes" in A46 in FIG. 4), the single-stranded region-extracting unit 21 sets the sequence structure as a sequence structure subjected to extraction (A47), and then, executes Step 42 and subsequent steps. Steps A47 to A46 via Step A42 are executed as long as a non-extracted sequence structure is present with respect to the same nucleotide sequence. If a non-extracted sequence structure is not present (corresponding to "no" in A46 in FIG. 4), (i.e. when a single-stranded region has been extracted with respect to all sequence structures corresponding to the same nucleotide sequence), then, the single-stranded region-extracting unit 21 sets a next nucleotide sequence other than the previously-set nucleotide sequence (A49), sets a sequence structure corresponding to this nucleotide sequence (A47), and executes Step 42 and subsequent steps. When extraction of a single-stranded region by the single-stranded region-extracting unit 21 is completed with respect to all inputted nucleotide sequences of nucleic acid molecules and all sequence structures corresponding to the nucleotide sequences, extraction of a single-stranded region in Step A4 is completed. In addition, information of the single-stranded region is classified according to the nucleotide sequence of each nucleic acid molecule, and is stored in the single-stranded region storage unit 34.

Then, the motif sequence-searching unit 22 utilizes information of the single-stranded region thus obtained in step A4, and searches a motif sequence from the single-stranded region, based on an evaluated value of the affinity of the nucleic acid molecule for the target substance (A5). The step of searching a motif sequence is not particularly limited as long as it is a step of searching a motif sequence based on an evaluated value, derived from each single-stranded region, of the nucleotide sequence of the nucleic acid molecule. As an example of the step, the step of searching a motif sequence is described below with reference to FIG. 5.

Figure 5:
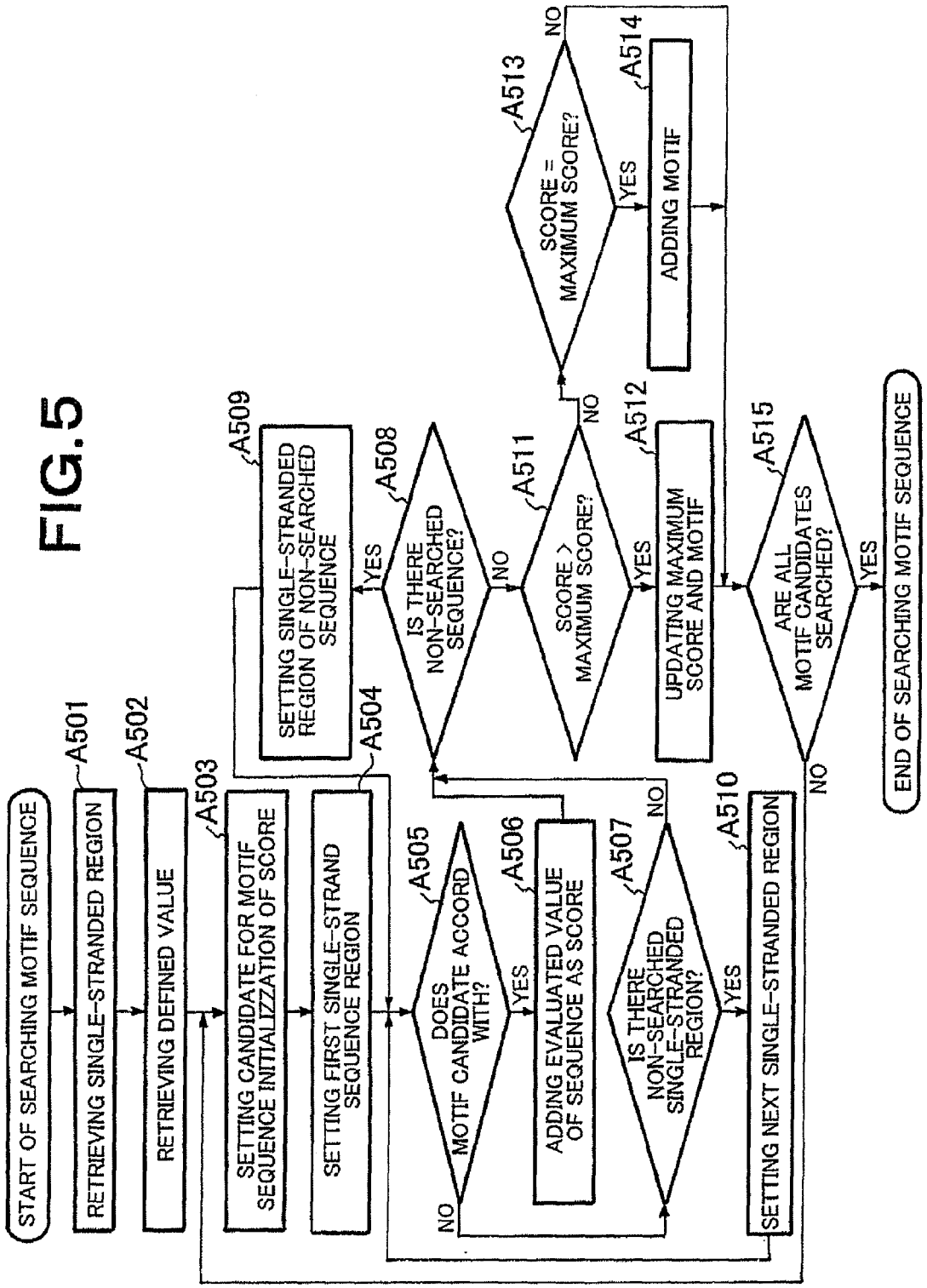
FIG. 5 is a flowchart showing an outline of searching a motif sequence.

FIG. 5 is a flowchart showing an outline of searching a motif sequence. The motif sequence-searching unit 22 retrieves information of the single-stranded region of the nucleotide sequence of each nucleic acid molecule stored in the single-stranded region storage unit 34 (A501). The motif sequence-searching unit 22 retrieves, from the defined value storage unit 31, defined values such as the length of a motif sequence to be searched in the step of searching a motif sequence, the number of mismatches negligible in this sequence, and an evaluated value indicating the affinity of the nucleic acid molecule for the target substance (A502).

Then, the motif sequence-searching unit 22 generates a sequence that agrees with conditions determined by the above-mentioned defined value concerning the motif sequence, and sets a first candidate for the motif sequence among candidates for the motif sequence (hereinafter, referred to as a "candidate for the motif sequence" or "motif candidate"). Generation of candidates for the motif sequence will be described later. In this generation, a plurality of candidates for the motif sequence is generally obtained. The motif sequence-searching unit 22 sets a variable as a score for the first set candidate for the motif sequence, and initializes the score (A503).

Now, one example of the method of generating candidates for the motif sequence by the motif sequence-searching unit 22 is described (A503). The candidate for the motif sequence to be set is expressed by combination of 5 letters of four bases (in the case of RNA, A, C, G and U) and symbol "." indicating a mismatch. With regard to the candidates for the motif sequence expressed in this manner, for example, the candidates for the motif sequence are further represented by a quinary number and decimal number of digits of the length of the motif sequence. Among these candidates, sequences including more mismatches than the number of negligible mismatches are excluded from targets to be searched by the motif sequence-searching unit, thereby achieving comprehensive searching of candidates for the motif sequence. Additionally, a "mismatch" may be construed as those having any one of bases of A, C, G and U or as being truncated. Furthermore, "mismatch" may also be construed as arbitrary combinations of A, C, G, U, and a truncated base (for example, as G and C or as A and U).

Then, when setting of the candidate for the motif sequence and initialization of the score are completed, the motif sequence-searching unit 22 sets, as a first searching target of the motif sequence, a first single-stranded region derived from a first sequence structure of the nucleotide sequence of the first nucleic acid molecule (A504).

Then, the motif sequence-searching unit 22 determines whether the first set candidate for the motif sequence accords with the first set single-stranded region (A505). If it is determined that the first set candidate for the motif sequence accords with the first set single-stranded region (corresponding to "yes" in A505 in FIG. 5), the motif sequence-searching unit 22 adds an evaluated, derived from the first single-stranded region, of the nucleotide sequence of the nucleic acid molecule to the score of the candidate for the motif sequence (A506). Thereafter, the motif sequence-searching unit 22 determines whether or not a non-searched nucleotide sequence of the nucleic acid molecule other than the nucleotide sequence corresponding to the first set single-stranded region is present (A508). If there is a non-searched nucleotide sequence of the nucleic acid molecule (corresponding to "yes" in A508 in FIG. 5), the motif sequence-searching unit 22 sets the first single-stranded region corresponding to the non-searched nucleotide sequence of the nucleic acid molecule (A509). Then, the motif sequence-searching unit 22 executes the same determination as described above in Step A505, and further executes the subsequent steps.

If the motif sequence-searching unit 22 determines in Step A505 that the first set candidate for the motif sequence does not accord with the first set single-stranded region (corresponding to "no" in A505 in FIG. 5), the motif sequence-searching unit 22 determines whether or not a non-searched single-stranded region is present in the nucleotide sequence of the nucleic acid molecule derived from the first set single-stranded region (A507). When it is determined that there is a non-searched single-stranded region (corresponding to "yes" in A507 in FIG. 5), the motif sequence-searching unit 22 sets this non-searched single-stranded region (A510), and determines whether the first set candidate for the motif sequence accords with the non-searched single-stranded region set herein (A505), and executes the subsequent steps.

As described above, the motif sequence-searching unit 22 performs a series of steps A505, A506, A508 and A509 and a series of steps A505, A507 and A510 until any non-searched candidate for the motif sequence and any non-searched single-stranded region no longer exist. If it is determined that a non-searched single-stranded region is not present (corresponding to "no" in A507) and it is simultaneously determined that a non-searched nucleotide sequence is not present (corresponding to "no" in A508), then, the motif sequence-searching unit 22 performs Step A511 and subsequent steps.

In Step A511, the motif sequence-searching unit 22 determines whether the score of the candidate for the motif sequence obtained by searching herein is larger than the maximum score stored in the defined value storage unit 31 (A511). When it is determined that the score of the candidate for the motif sequence is larger than the maximum score (corresponding to "yes" in A511 in FIG. 5), the motif sequence-searching unit 22 rewrites the maximum score stored in the defined value storage unit 31, and allows the candidate for the motif sequence to be stored as a motif sequence in the motif sequence storage unit 35 (A512). If it is determined that the score of the candidate for the motif sequence is not larger than the maximum score (corresponding to "no" in A511 in FIG. 5), then, the motif sequence-searching unit 22 determines whether this score is the same value as the maximum score (A513). If it is determined that the score is the same value (corresponding to "yes" in A513 in FIG. 5), the motif sequence-searching unit 22 allows the candidate for the motif sequence to be stored in the motif sequence storage unit 35 as one of motif sequences. In this case, the maximum score stored in the defined value storage unit 31 is not updated.

If Step A512 or A514 is completed or If it is determined in Step A513 that the score is not the same value as the maximum score (corresponding to "no" in A513 in FIG. 5), the motif sequence-searching unit 22 determines whether searching is completed with respect to all candidates for the motif sequence generated in A503 (A515). If it is determined that searching is not completed with respect to all candidates for the motif sequence (corresponding to "no" in A515 in FIG. 5), the motif sequence-searching unit 22 sets a next candidate for the motif sequence, initializes the score of this candidate for the motif sequence, and performs Step A504 and subsequent steps. When it is determined that searching is completed with respect to all candidates for the motif sequence (corresponding to "yes" in A515 in FIG. 5), searching of candidates for the motif sequence is completed.

In Step A5, single-stranded regions of the sequences may be subjected to multiple alignment, and PWM (positional weight matrix) may be prepared with respect to a particularly-conserved region. The value obtained by counting as to which base is present at a certain position of residue from the terminal with respect to each single-stranded region obtained in Step A4 may be weighted with a defined value such as an evaluated value stored in the defined value storage unit 31 to obtain the motif sequence. If Step A5 is performed in this manner, a weight at a specific position of each base may be calculated according to the following equation:

$$\text{Weight}_{i,j} = \ln(((n_{i,j} + p_i)/(N+1))/p_i)$$

$n_{i,j}$: frequency of appearance of base i at position j in each single-stranded region
$p_i$: priori probability of base i
N: number of single-stranded regions to be examined.

When accurately aligned sequences are obtained in the above-mentioned multiple alignment, only one motif sequence expressed by PWM can be obtained. Accordingly, the processing can be conducted at a relatively-high speed.

When Steps A1 to A5 are completed in this manner, the steps in the method for identifying a nucleotide sequence according to the present invention are completed, thereby identifying a motif sequence included in the nucleotide sequence of the nucleic acid molecule having affinity for the target substance. Furthermore, the maximum score corresponding to this motif sequence is obtained. All information including these is outputted to the output device 4.

Thus, according to the method for identifying a nucleotide sequence, the apparatus for identifying a nucleotide sequence and the program for identifying a nucleotide sequence of the present invention, a motif sequence included in a nucleotide sequence of a nucleic acid molecule having affinity for a target substance can be identified, and also, the maximum score corresponding to this motif sequence can be obtained. The maximum score obtained herein is considered as an index indicating the affinity of the motif sequence for the target substance, and it can also be understood that the motif sequence corresponding to the maximum score be useful as a molecular species having high affinity for the target substance. When a motif sequence having a higher score than the maximum score is discovered at this time, the maximum score is updated, and only one motif sequence corresponding to the maximum score is finally outputted, as described above. However, alternatively, the scores corresponding to the respective motif sequences are stored in the motif sequence storage unit 35, and the motif sequences aligned according to score may be identified as sequences compared with one another in the magnitude of affinity for the target substance.

<The Method for Acquiring a Secondary Structure of a Nucleic Acid Molecule, the Apparatus for Acquiring a Secondary Structure of a Nucleic Acid Molecule and the Program for Acquiring a Secondary Structure of a Nucleic Acid Molecule According to the Present Invention>

<Configuration of the Apparatus for Identifying a Secondary Structure of a Nucleic Acid Molecule According to the Present Invention, Function of Each Component, Etc.>

Hereinafter, with reference to FIG. 1B, the configuration of the apparatus for identifying a secondary structure of a nucleic acid molecule according to the present invention will be described. FIG. 1B is a schematic diagram of the apparatus for identifying a secondary structure of a nucleic acid molecule according to the present invention. The apparatus for identifying a secondary structure of a nucleic acid molecule according to the present invention, similar to the above-described apparatus for identifying a nucleotide sequence according to the present invention, includes an input device 1, a data-processing device 2, a storage device 3, and an output device 4. In the apparatus for acquiring a secondary structure of a nucleic acid molecule according to the present invention, the date-processing unit 2 includes a general structure-acquiring unit 23 besides the single-stranded region-extracting unit 21 and the motif sequence-searching unit 22. In the apparatus for acquiring a secondary structure of a nucleic acid molecule according to the present invention, the storage device 3 includes a defined value storage unit 31, a sequence storage unit 32, a sequence structure storage unit 33, a single-stranded region storage unit 34, and a motif sequence storage unit 35.

The single-stranded region-extracting unit 21, the motif sequence-searching unit 22, the defined value storage unit 31, the sequence storage unit 32, the sequence structure storage unit 33, the single-stranded region storage unit 34 and the motif sequence storage unit 35 have the same functions as described above. Therefore, their description is omitted herein.

In the apparatus for acquiring a secondary structure of a nucleic acid molecule according to the present invention, the data-processing device 2 includes a general structure-acquiring unit 23. The general structure-acquiring unit 23 acquires a general structure from a secondary structure of a nucleic acid molecule, which is a target for acquisition of the secondary structure, based on a single-stranded region that accords with a motif sequence searched (identified) by the motif sequence-searching unit 22 and bases forming a stem structure positioned at both ends of the single-stranded region. For example, the general structure-acquiring unit 23 first retrieves information of each nucleotide sequence from the sequence storage unit 32, information of sequence structures such as a secondary structure corresponding to this nucleotide sequence from the sequence structure storage unit 33, information of a single-stranded region corresponding to this sequence structure from the single-stranded region storage unit 34, and information of a motif sequence corresponding to this nucleotide sequence from the motif sequence storage unit 35, respectively. Then, the general structure-acquiring unit 23 examines whether the single-stranded region of each nucleotide sequence accords with the motif sequence, and detects a single-stranded region corresponding to the motif sequence. With respect to the nucleotide sequence having a single-stranded region that accords with the motif sequence, the information of the nucleotide sequence and the information of the sequence structure corresponding to the nucleotide sequence are referenced, and the secondary structure of the nucleic acid molecule is obtained as a general structure, based on the single-stranded region that accords with this motif sequence and a stem structure positioned at both ends of this single-stranded region, and this general structure is outputted to the output device 4. In this case, from the secondary structure of the nucleotide sequence of the nucleic acid molecule including the single-stranded region that accords with this motif sequence, the general structure-acquiring unit 23 may obtain a general structure of the nucleotide sequence corresponding to bases having in the center this single-stranded region and a stem structure positioned at both ends of this single-stranded region, and may output the acquired general structure. Furthermore, from the secondary structure of the nucleotide sequence of the nucleic acid molecule including the single-stranded region that accords with this motif sequence, the general structure-acquiring unit 23 may acquire a general structure of the nucleotide sequence corresponding to bases having in the center this motif sequence and the stem structure positioned at both ends of the single-stranded region that accords with the motif sequence, and may output the general structure to the output device 4.

In the step of acquiring the general structure from the secondary structure of the nucleic acid molecule as the target according to the general structure-acquiring unit 23, the term "center" in "bases having in the center the single-stranded region and the stem structure positioned at both ends of the single-stranded region" means that the single-stranded region is positioned around the central of the obtained general structure, including the case where the region formed of the single-stranded region and the stem structure is present in a portion of the general structure where the structure becomes symmetrical. Therefore, in the present invention, the obtained general structure is not particularly limited as long as the general structure is based on the single-stranded region and bases constituting the stem structure positioned at both ends of the single-stranded region. That is, the term "center" refers to one embodiment of the obtained general structure.

(Steps in the Method for Acquiring a Secondary Structure of a Nucleic Acid Molecule and the Program for Acquiring a Secondary Structure of a Nucleic Acid Molecule According to the Present Invention, Actuation of the Apparatus for Acquiring a Secondary Structure of a Nucleic Acid Molecule According to the Present Invention)

Hereinafter, with reference to FIG. 1B, FIG. 3B, FIG. 6, etc., the steps in the method for acquiring a secondary structure of a nucleic acid molecule and the program for acquiring a secondary structure of a nucleic acid molecule according to the present invention, actuation of the apparatus for acquiring a secondary structure of a nucleic acid molecule according to the present invention, etc. will be described in detail. Steps A1 to A5 shown in FIG. 3B, Steps A41 to A49 shown in FIG. 4 corresponding to Step A4 in FIG. 3B, and Steps A501 to A515 shown in FIG. 5 corresponding to Step A5 in FIG. 3B are the same as described in the method for identifying a nucleotide sequence according to the present invention. Therefore, their description is omitted to avoid repetition. Accordingly, Step 6 and subsequent steps shown in FIG. 3B and Steps A61 to A69 in FIG. 6 are mainly described.

In Step A6, the general structure-acquiring unit 23 is utilized to detect, as a general structure, the secondary structure of the nucleotide sequence including the motif sequence obtained in Steps A1 to A5 (A6). Acquisition of the general structure is described with reference to FIG. 6.

Figure 6:
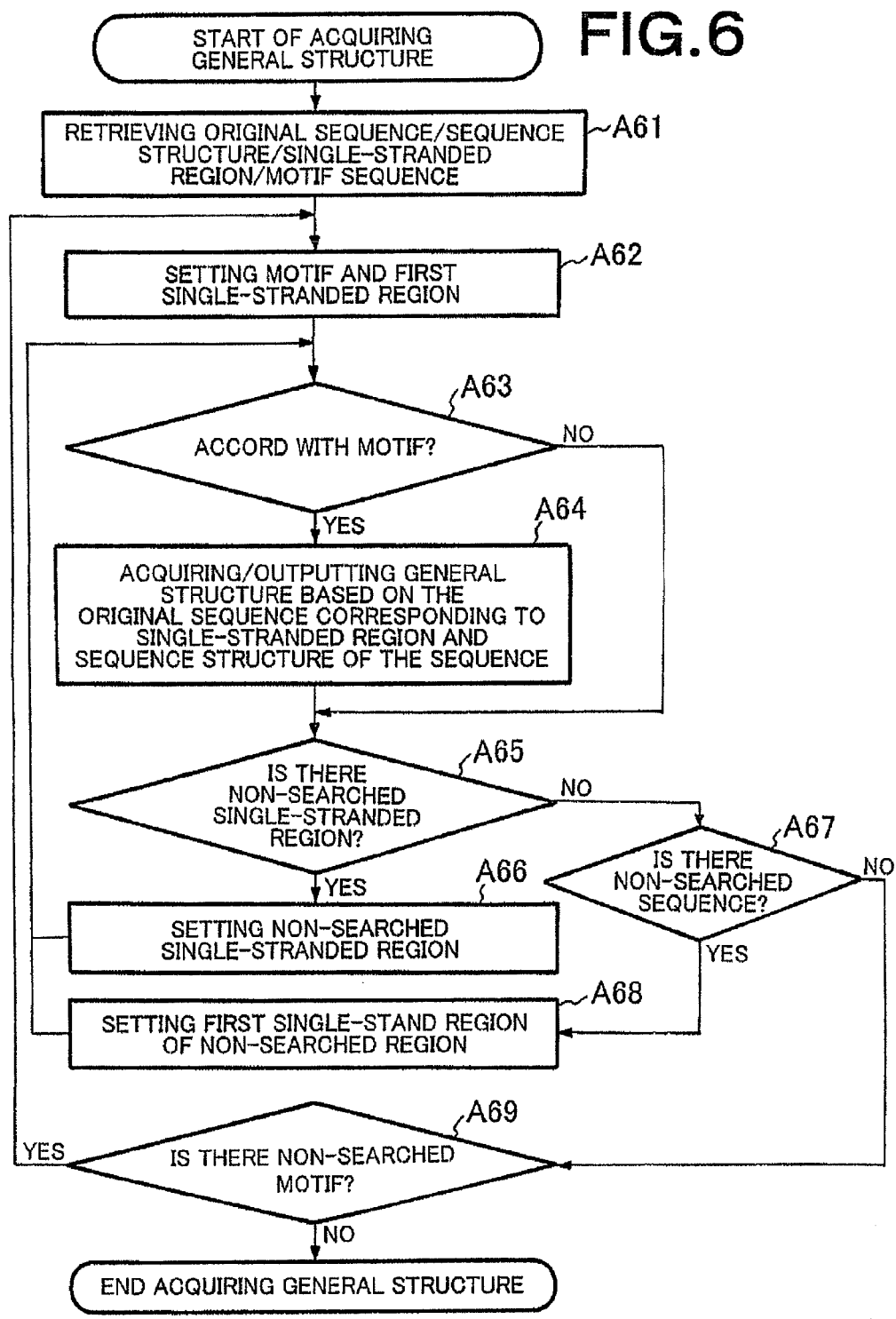
FIG. 6 is a flowchart showing an outline of acquiring a general structure.

FIG. 6 is a flowchart showing an outline of acquisition of the general structure. The general structure-acquiring unit 23 first retrieves information of the nucleotide sequence (original sequence) from the sequence storage unit 32, information of the sequence structure of the original sequence from the sequence structure storage unit 33, information of a single-stranded region corresponding to the sequence structure from the single-stranded region storage unit 34, and information of a motif sequence identified from this nucleotide sequence from the motif sequence storage unit 35, respectively (A61). Then, the general structure-acquiring unit 23 sets the first motif sequence and the first single-stranded region of the first original sequence (A62), and determines whether the first single-stranded region and this motif sequence accord with each other (A63).

If the general structure-acquiring unit 23 determines in A63 that the motif sequence accords with the single-stranded region, this means that the general structure-acquiring unit 23 detects the single-stranded region that accords with the motif sequence. Then, by referencing the original sequence corresponding to the single-stranded region and the sequence structure corresponding to this original sequence, the general structure-acquiring unit 23 obtains, from the sequence structure of the original sequence, a general structure such as a secondary structure corresponding to bases having in the center the single-stranded region that accords with motif sequence and a stem structure necessary for forming this single-stranded region (i.e. a stem structure formed of bases positioned at both ends of this single-stranded region) (A64). This general structure is a general structure obtained in Step A63. The general structure-acquiring unit 23 may output the general structure to the output device 4 (A64).

Additionally, in A64, the general structure-acquiring unit 23 may acquire the general structure by replacing the single-stranded region corresponding to the motif sequence with this motif sequence. That is, in A64, by referencing the original sequence corresponding to the single-stranded region which is assessed to accord with the motif sequence and the sequence structure corresponding to the original sequence, the general structure-acquiring unit 23 may acquire, from the general structure of the original sequence, the general structure of the original sequence corresponding to the bases having in the center the single-stranded region which is assessed to accord with the motif sequence and the stem structure necessary for forming the single-stranded region, and may acquire a general structure obtained by replacing the region corresponding to the single-stranded region of the general structure with the motif sequence.

After the acquisition/output in A64 is completed, or when it is determined in A63 that there is no single-stranded region corresponding to the motif sequence, the general structure-acquiring unit 23 determines whether or not a non-searched single-stranded region is present in the original sequence (A65). If a non-searched single-stranded region is present, the general structure-acquiring unit 23 sets the new single-stranded region as a target to be searched (A66), and executes Step A63 and subsequent steps in the same manner as described above. If it is determined that there is no non-searched single-stranded region, then, the general structure-acquiring unit 23 determines whether or not a non-searched original sequence is present (A67). If there is a non-searched original sequence, the general structure-acquiring unit 23 sets the first single-stranded region of the non-searched original sequence as a searching target (A68), and determines whether or not a motif sequence is present in the sequence (A63). If it is determined that there is no non-searched original sequence, the general structure-acquiring unit 23 determines whether or not a non-searched motif sequence is present (A69). If a non-searched motif sequence is present, the general structure-acquiring unit 23 sets this non-searched motif sequence and the first single-stranded region of the first original sequence as searching targets (A62), and subsequent steps are repeated in the same procedure as described above. This procedure is repeated as long as a non-sequenced motif sequence is present. When a non-searched motif sequence is not present, the step of acquiring the general structure is completed.

When Steps A1 to A6 are completed in this manner, all steps of the method for acquiring a secondary structure of a nucleic acid molecule according to the present invention are completed, whereby the secondary structure of a nucleic acid molecule including a motif sequence included in a nucleotide sequence of the nucleic acid molecule having affinity for a target substance is obtained.

Accordingly, according to the method for acquiring a secondary structure of a nucleic acid molecule, the apparatus for acquiring a secondary structure of a nucleic acid molecule, and the program for acquiring a secondary structure of a nucleic acid molecule according to the present invention, a secondary structure of a nucleic acid molecule including a motif sequence included in a nucleotide sequence of a nucleic acid molecule having affinity for a target substance can be obtained. Based on this secondary structure, a minimum structure having affinity for the target substance can be efficiently synthesized.

<Other Components>

Hereinafter, other components that may be included in the present invention will be described in detail.

(Secondary Structure-Predicting Unit)

In the present invention, the data-processing device 2 may include a secondary structure-predicting unit 24 that has a function of predicting bases capable of forming a stem structure in a nucleotide sequence of a nucleic acid molecule. FIG. 1C is a schematic diagram showing one example of the apparatus for identifying a nucleotide sequence according to the present invention, which has such a secondary structure-predicting unit. FIG. 1D is a schematic diagram showing one example of the apparatus for acquiring a secondary structure of a nucleic acid molecule according to the present invention, which also has such a secondary structure-predicting unit. That is, the secondary structure-predicting unit 24 predicts bases capable of forming complementary base pairs (stem structure) such as A and U or G and C among the bases constituting a nucleotide sequence of a nucleic acid molecule that is inputted through the input device 1. The secondary structure-predicting unit 24 may also predict a sequence structure such as a secondary structure that can be formed in the nucleotide sequence of a nucleic acid molecule, based on the above-predicted bases. The information of sequence structure such as a secondary structure predicted by the secondary structure-predicting unit 24 is stored as a sequence structure in the sequence structure storage unit 33. Therefore, in the present invention, the information of sequence structure obtained by the secondary structure-predicting unit 24 may be used instead of inputting, through the input device 1, sequence structures such as results of a secondary structure corresponding to the nucleotide sequence of the nucleic acid molecule. The above step using the secondary structure-predicting unit 24 is a step conducted instead of Step A2, and may be conducted until Step A4.

(Random Region-Extracting Unit)

Figure 1E:
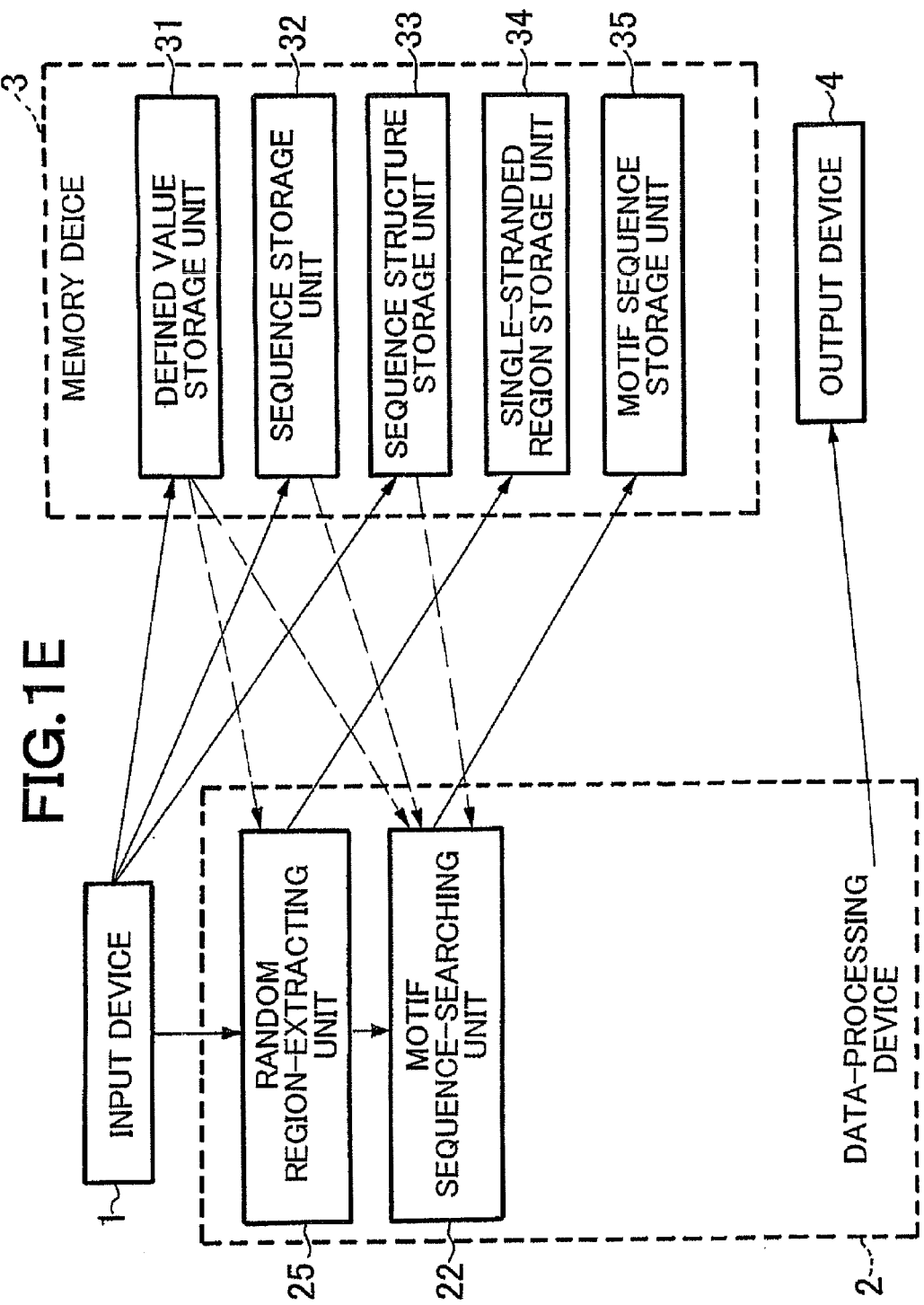
FIG. 1E is a schematic diagram showing an example of the apparatus for identifying a nucleotide sequence according to the present invention that includes a random region-extracting unit.

In the present invention, the data-processing device 2 may include a random region-extracting unit 25 which extracts a random region from a nucleotide sequence of a nucleic acid molecule, instead of the single-stranded region-extracting unit 21. FIG. 1E is a schematic diagram showing one example of the apparatus for identifying a nucleotide sequence according to the present invention, which includes such a random region-extracting unit. FIG. 1F is a schematic diagram showing one example of the apparatus for acquiring a secondary structure of a nucleic acid molecule according to the present invention, which includes such a random region-extracting unit. As described above, the single-stranded region-extracting unit 21 extracts a single-stranded region from the nucleotide sequences of nucleic acid molecules inputted through the input device 1 by excluding bases capable of forming a stem structure. However, if the random region-extracting unit 25 is utilized, the whole region of the inputted nucleotide sequence of the nucleic acid molecule is subjected to searching without excluding bases capable of forming a stem structure from the inputted nucleotide sequence of nucleic acid molecule. Accordingly, when the random region-extracting unit 25 is utilized instead of the single-stranded region-extracting unit 21, the method for identifying a nucleotide sequence and the method for acquiring a secondary structure of a nucleic acid molecule according to the present invention are as follows.

The method for identifying a nucleotide sequence according to the present invention is a method for identifying a nucleotide sequence necessary for expressing affinity for a target substance in a nucleotide sequence of a nucleic acid molecule having such affinity, the method including the steps of: extracting a random region from the nucleotide sequence of the nucleic acid molecule; and searching a motif sequence from the random region, based on an evaluated value of the affinity.

The method for acquiring a secondary structure of a nucleic acid molecule according to the present invention is a method for acquiring a secondary structure of a nucleic acid molecule including a nucleotide sequence necessary for expressing affinity for a target substance in a nucleotide sequence of a nucleic acid molecule having such affinity, the method including the steps of: extracting a random region from the nucleotide sequence of nucleic acid molecule; searching a motif sequence from the random region, based on an evaluated value of the affinity; and acquiring a general structure from a secondary structure of the nucleic acid molecule, based on the random region which accords with the motif sequence.

In this case, in order to conduct the step of "searching a motif sequence from the random region, based on an evaluated value of the affinity", the step of using the motif sequence-searching unit 22 may be conducted by replacing "the single-stranded region" with "the random region" in the above description.

In order to conduct the step of "acquiring a general structure from a secondary structure of the nucleic acid molecule, based on the random region corresponding to the motif sequence", the step of using the general structure-acquiring unit 23 may be conducted by replacing "the single-stranded region" with "the random region". When this step is conducted using the general structure-acquiring unit 23, the "general structure" may be appropriately set depending on which site the bases constituting the random region is present in sequence structures such as secondary structure of the nucleotide sequence of the nucleic acid molecule. For example, when the bases constituting the random region forms a single-stranded region such as a loop structure other than a stem structure in a sequence structure of the nucleotide sequence of the nucleic acid molecule, the general structure may be obtained as a secondary structure corresponding to bases having in the center the signal-stranded region including this random region and the stem structure necessary for forming this single-stranded region. When the bases constituting the random region correspond to bases constituting the stem structure in a sequence structure of the nucleotide sequence of the nucleic acid molecule, the general structure may be obtained as a secondary structure corresponding to the bases constituting the stem structure, or may be obtained as a secondary structure corresponding to bases constituting the stem structure and bases complementary to these bases. When the bases constituting the random region span both bases constituting a single-stranded region such as a loop region other than a stem structure and bases constituting the stem structure necessary for forming this single-stranded region in the sequence structure of the nucleotide sequence of the nucleic acid molecule, the general structure may be obtained as a secondary structure corresponding to the single-stranded region including the random region and bases corresponding to the stem structure necessary for forming the single-stranded region. Accordingly, in either case, the secondary structure of the nucleic acid molecule obtained as the general structure includes the motif sequence.

If the random region-extracting unit 25 is utilized instead of the single-stranded region-extracting unit 21, the apparatus for identifying a nucleotide sequence and the apparatus for acquiring a secondary structure of a nucleic acid molecule according to the present invention, and the program for identifying a nucleotide sequence and the program for acquiring a secondary structure of a nucleic acid molecule according to the present invention are as follows.

The apparatus for identifying a nucleotide sequence according to the present invention is an apparatus for identifying a nucleotide sequence necessary for expressing affinity for a target substance in nucleotide sequences of nucleic acid molecules having such affinity, the apparatus including: a random region-extracting unit that extracting a random region from a nucleotide sequence of a nucleic acid molecule; and a motif sequence-searching unit that searches a motif sequence from the random region, based on an evaluated value of the affinity.

The apparatus for acquiring a secondary structure of a nucleic acid molecule according to the present invention is an apparatus for acquiring a secondary structure of a nucleic acid molecule including a nucleotide sequence necessary for expressing affinity for a target substance, in nucleotide sequences of nucleic acid molecules having such affinity, the apparatus including: a random region-extracting unit that extract a random region from the nucleotide sequence of nucleic acid molecule; a motif sequence-searching unit that searches a motif sequence from the random region, based on an evaluated value of the affinity; and a general structure-acquiring unit that acquires a general structure from a secondary structure of the nucleic acid molecule, based on the random region that accords with the motif sequence.

The program for identifying a nucleotide sequence according to the present invention is a program for identifying a nucleotide sequence necessary for expressing affinity for a target substance, in nucleotide sequences of nucleic acid molecules having such affinity, the program executing the steps of: extracting a random region from the nucleotide sequence of nucleic acid molecule; and searching a motif sequence from the random region, based on an evaluated value of the affinity.

The program for acquiring a secondary structure of a nucleic acid molecule according to the present is a program for acquiring a secondary structure of a nucleic acid molecule including a nucleotide sequence necessary for expressing affinity for a target substance in nucleotide sequences of nucleic acid molecules having such affinity, the program executing the steps of: extracting a random region from the nucleotide sequence of the nucleic acid molecule; searching a motif sequence from the random region, based on an evaluated value of the affinity; and acquiring a general structure from a secondary structure of the nucleic acid molecule, based on the random region corresponding to the motif sequence.

EXAMPLES

Hereinafter, the present invention will be described with reference to Examples.

Example 1

At first, when the sequence (sequence 1, SEQ ID NO: 1) shown in FIG. 7 and its structures (structures 1-1 and 1-2) were input through the input device 1, the information was stored in a sequence storage unit 32 and sequence structure storage unit 33 (A1, A2, A3), and the information and initial values of defined values stored previously in the defined value storage unit 31 were transmitted to the single-stranded region-extracting unit 21.

The single-stranded region-extracting unit 21 first set sequence 1 (SEQ ID NO: 1) and structure 1-1 as the first target for the single-stranded region-extraction (A41). After bases corresponding to a primer region were removed (A42, A43), bases (bases corresponding to sites shown with "(" and ")" in each structure) forming base pairs in the sequence were replaced by blanks (A44). Consequently, the single-stranded region 1-1 (FIG. 8, SEQ ID NO: 3) was stored in the single-stranded region storage unit 34 (A45). Since two structures (structures 1-1 and 1-2) had been inputted with respect to sequence 1, subsequently, sequence 1 and structure 1-2 were set (A46, A47), and a single-stranded region 1-2 (FIG. 8, SEQ ID NO: 3) was stored in the single-stranded region storage unit 34 in the same manner as for structure 1-1. At this point, a single-stranded region had been already extracted from every structure of sequence 1. Then, sequence 2 (FIG. 7, SEQ ID NO: 2) was subjected to the same processing as described above (A48, A49). Consequently, the single-stranded region 2-1 (FIG. 8, SEQ ID NO: 4) and the single-stranded region 2-2 (FIG. 8, SEQ ID NO: 4) were stored in the single-stranded region storage unit 34. After this operation was completed, the single-stranded regions as shown in FIG. 8 had been stored in the single-stranded region storage unit 34.

The motif sequence-searching unit 22 retrieved information of a single-stranded region stored in the single-stranded region storage unit 34 and information of a defined value stored in the defined value storage unit 31 (A501, A502). In this case, it was assumed that the length of a searched motif sequence stored as defined value was 4, the number of negligible mismatches was 1, the initial value of the maximum score was 0.1, and the evaluated values of the binding affinity of sequences 1 and 2 to a target substance were 1. Then, the motif sequence-searching unit 22 set "AAAA" as a first candidate for the motif sequence. The score of this candidate for the motif sequence was initialized to 0 (A503), and then, the single-stranded region 1-1 was set as the first single-stranded region (A504). The single-stranded region "AAAA" that accorded with the first set candidate for the motif sequence was present in the single-stranded region 1-1. Therefore, the value of "1", which was the above-mentioned evaluated value of the binding affinity of sequence 1, was added to the score of this candidate for the motif sequence (A505, A506). Since it was found that the candidate for the motif sequence candidate was present in sequence 1, searching a motif candidate was not performed with respect to the non-searched single-stranded region 1-2 of sequence 1. As the next searching region, the single-stranded region 2-1 that was a first single-stranded region of sequence 2 was set (A508, A509). Since the first set candidate for the motif sequence of "AAAA" was not present in the single-stranded region 2-1 (corresponding to "no" in A505), the single-stranded region 2-2 that was a non-searched single-stranded region of sequence 2 was subsequently set (A505, A507, A510). In the same manner, since the candidate for the motif sequence of "AAAA" was not present in the single-stranded region 2-2, and a non-searched sequence no longer existed therein, determination of the score was performed (A508, A511, A513). At this time, the score of the candidate for the motif sequence of "AAAA" was 1. That is, the score was higher than the value of 0.1, which was the maximum score at that time. Therefore, the value of 1 was stored as the maximum score in the defined value storage unit 31 while "AAAA" was stored as the motif sequence in the motif sequence storage unit 35 (A512). After that, "AAAC" was set as a new candidate for the motif sequence, and the score of this candidate for the motif sequence was initialized to 0, and the initial single-stranded region 1-1 was set (A515, A503, A504). Thereafter, the same processing was repeated as described above until evaluation of patterns in all motif sequences that agreed with the conditions of defined values was completed (A515). In this case, the candidate for the motif sequence that was finally stored in the motif sequence storage unit 35 as a motif sequence was "A. AA" (SEQ ID NO: 5) where only the candidate for the motif sequence had a score of 2 among all cases. In this manner, the motif sequence included in the nucleotide sequences (sequences 1 and 2) of the nucleic acid molecule could be obtained.

Example 2

Figure 9:
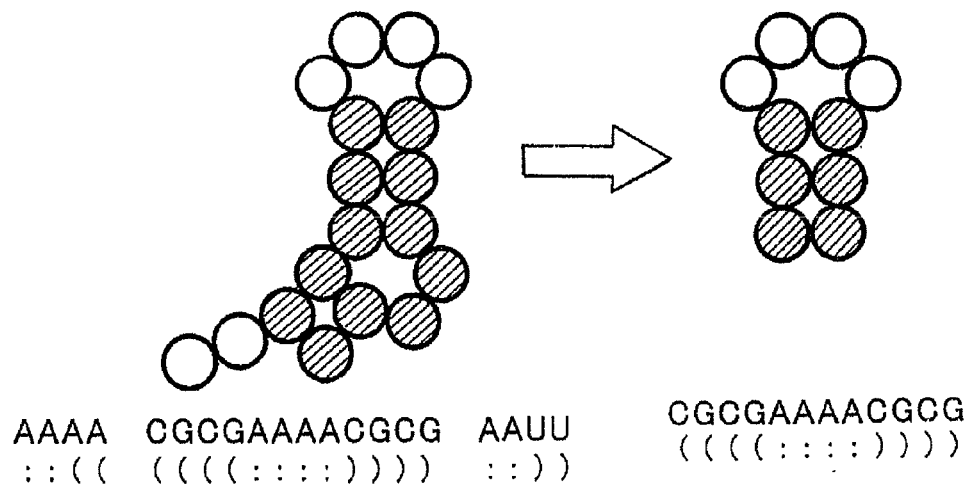
FIG. 9 shows an example of a general structure obtained for Sequence 1 (SEQ ID NO: 1) in FIG. 7.

Then, the general structure-acquiring unit 23 retrieved information of each of the sequence, structure, single-stranded region and motif sequence obtained in Example 1 from the sequence storage unit 32, the sequence structure storage unit 33, the single-stranded region storage unit 34 and the motif sequence storage unit 35 respectively (A61), and set the motif sequence of "A. AA" and the first single-stranded region 1-1 (A62). Since the motif sequence "A. AA" was present in the single-stranded region 1-1, a secondary structure (general structure) formed such that the structure had in the center a motif sequence-including loop site and a stem structure necessary for forming the loop site was outputted to the output device 4 with respect to sequence 1 and structure 1-1 corresponding to the single-stranded region 1-1. Specifically, the general structure (whose nucleotide sequence is SEQ ID NO: 6) shown in the right side of FIG. 9 was outputted with respect to structure 1-1 (A63, A64). Hereinafter, whether or not motif sequence "A. AA" is present was determined with respect to all the single-stranded regions of all the sequences, and the general structures whose sequences included a motif sequence were outputted to the output device 4. Those wherein the bases corresponding to SEQ ID NO: 1 in the general structure corresponding to the sequence shown in SEQ ID NO: 6 were replaced with the motif sequence "A. AA" were output as general structures.

Example 3

Figure 10:
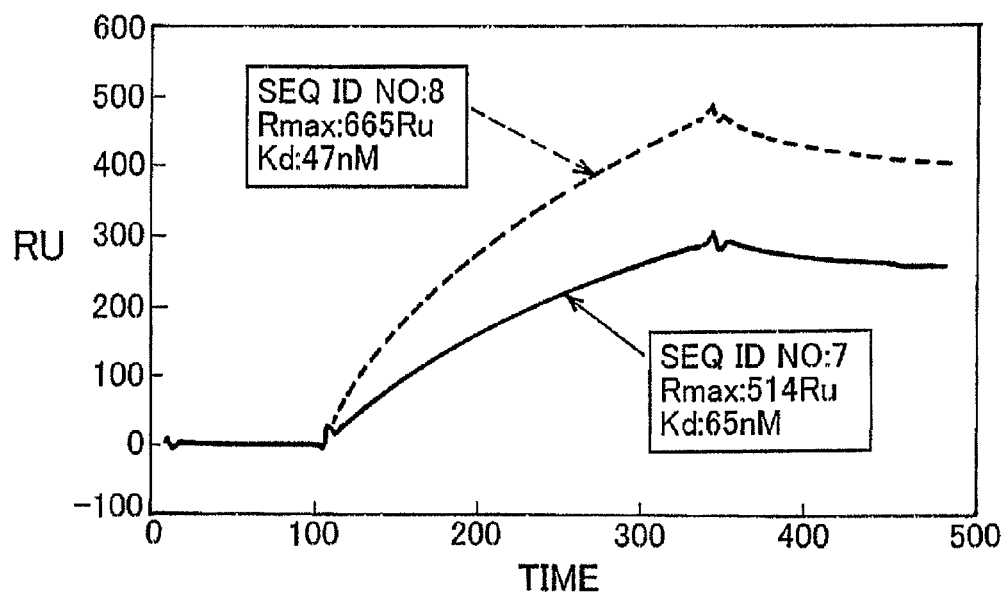
FIG. 10 shows comparison between an aptamer obtained for IgG and its general structure obtained by the present invention with regard to the binding affinity.

With respect to the sequence (seventy-four residues) shown in SEQ ID NO: 7, a general structure of the sequence (forty residues) shown in SEQ ID NO: 8 was obtained according to the method for acquiring a secondary structure of a nucleic acid according to the present invention. The sequences shown in SEQ ID NOS: 7 and 8 were subjected to binding assay with BIACORE 2000. The results are shown in FIG. 10. According to FIG. 10, both Rmax and Kd values of the sequence of SEQ ID NO: 8, which showed higher binding affinity as an aptamer than the sequence of SEQ ID NO: 7, were obtained. This means that the present invention is quite effective for acquiring the general structure of an aptamer.

The present invention has been particularly shown and described with reference to preferable embodiments thereof. The present invention has been described with reference to specific example. However, it is apparent that various changes in form and details may be made therein without departing from the spirit and scope of the present invention as defined by the claims. That is, it should not be understood that the present invention be limited by details of the specific examples and the accompanying drawings.

INDUSTRIAL APPLICABILITY

It can be understood that the present invention be applied to a process wherein a redundant site of an aptamer obtained by the SELEX method is eliminated to extract an important site of the aptamer. According to the present invention, an approach of information science can be applied to a process of extracting an important site of an aptamer which an experimental method only has conventionally been applicable to. The present invention may be combined with the conventional experimental method to achieve a more accurate method for extracting an important site, or may be used instead of the experimental method in order to reduce labor.

The invention claimed is:

1. A method for preparing an optimized aptamer sequence, comprising:
   (a) screening nucleic acids by identifying a region within a nucleic acid molecule that binds to a target substance; wherein said identifying comprises the steps of:
       (1) extracting data of a single-stranded region, by excluding bases capable of forming a stem structure from the sequence of the nucleic acid molecule; and
       (2) searching a motif sequence from the single-stranded region, by weighing the appearance frequency of a specific sequence in the extracted data with an evaluated value of the affinity of the nucleic acid molecule for the target substance,
       wherein steps (1) and (2) are performed using a data processing device comprising a hardware processor and non-transitory computer-readable medium, said medium comprising one or more programs, executed by the hardware processor, which comprise commands for:
       extracting data of the single-stranded region; and
       searching the motif sequence from the single-stranded region;
   (b) preparing an aptamer sequence that contains the region binding to the target substance, but which lacks one or more corresponding nucleotides that are present in the nucleic acid molecule and which are unnecessary for binding to the target substance; and
   (c) outputting the prepared aptamer sequence.

2. The method of claim 1, wherein said method for identifying the region further comprises a step of predicting the bases in said nucleic acid molecule that are capable of forming a stem structure.

3. The method of claim 1, wherein the step of searching a motif sequence is a step in which, when the single-stranded region that accords with any one of a plurality of candidates for the motif sequence is detected, an evaluated value of the nucleotide sequence corresponding to the single-stranded region is added as a score to the candidate for the motif sequence that accords with the single-stranded region, and a candidate for the motif sequence having the largest score is assessed as the motif sequence.

4. The method of claim 1, wherein the evaluated value is a value defined based on a binding constant between the target substance and the nucleic acid molecule.

5. The method of claim 1, further comprising synthesizing an aptamer molecule with the prepared aptamer sequence.

6. The method of claim 5, wherein said aptamer is synthesized by chemical synthesis.

7. An apparatus for preparing an optimized aptamer sequence, wherein said apparatus comprises a data processing device comprising a hardware processor and non-transitory computer-readable medium, said medium comprising one or more programs, executed by the hardware processor, which comprise commands for:
   (1) extracting data of a single-stranded region, by excluding bases capable of forming a stem structure from the sequence of the nucleic acid molecule; and
   (2) searching a motif sequence from the single-stranded region, by weighing the appearance frequency of a specific sequence in the extracted data with an evaluated value of the affinity of the nucleic acid molecule for the target substance,
   and wherein said apparatus is configured to prepare and output an aptamer sequence that contains the region binding to the target substance, but which lacks one or more corresponding nucleotides that are present in the nucleic acid molecule and which are unnecessary for binding to the target substance.

8. The apparatus of claim 7, wherein said one or more programs further comprise commands for predicting the bases in said nucleic acid molecule that are capable of forming a stem structure.

9. The apparatus of claim 7, wherein, when the single-stranded region that accords with any one of a plurality of candidates for the motif sequence is detected, an evaluated value of the nucleotide sequence corresponding to the single-stranded region is added as a score to the candidate for the motif sequence corresponding to the single-stranded region, and a candidate for the motif sequence having the largest score is assessed as the motif sequence.

10. An apparatus for preparing an optimized aptamer sequence, wherein said apparatus comprises a data processing device comprising a hardware processor and non-transitory computer-readable medium, said medium comprising one or more programs, executed by the hardware processor, which comprise commands for:
   (1) extracting data of a single-stranded region, by excluding bases capable of forming a stem structure from the sequence of the nucleic acid molecule;
   (2) searching a motif sequence from the single-stranded region, by weighing the appearance frequency of a specific sequence in the extracted data with an evaluated value of the affinity of the nucleic acid molecule for the target substance; and
   (3) acquiring a general structure from a secondary structure of the nucleic acid molecule, based on the single-stranded region that accords with the motif sequence and based on bases forming the stem structure positioned at both ends of the single-stranded region,
   and wherein said apparatus is configured to prepare and output an aptamer sequence that contains the region binding to the target substance, but which lacks one or more corresponding nucleotides that are present in the nucleic acid molecule and which are unnecessary for binding to the target substance.

11. A method for preparing an optimized aptamer sequence, comprising:
(a) screening nucleic acids by acquiring a secondary structure of a nucleic acid molecule that contains a region that binds to a target substance; wherein said acquiring comprises the steps of:
(1) extracting data of a single-stranded region by excluding bases capable of forming a stem structure from the sequence of the nucleic acid molecule;
(2) searching a motif sequence from the single-stranded region, by weighing the appearance frequency of a specific sequence in the extracted data with an evaluated value of the affinity of the nucleic acid molecule for the target substance; and
(3) acquiring a general structure from a secondary structure of the nucleic acid molecule, based on the single-stranded region that accords with the motif sequence and based on bases forming the stem structure positioned at both ends of the single-stranded region,
steps (1)-(3) are performed using the apparatus of claim 10;
(b) preparing an aptamer sequence that contains the region binding to the target substance, but which lacks one or more corresponding nucleotides that are present in the nucleic acid molecule and which are unnecessary for binding to the target substance; and
(c) outputting the prepared aptamer sequence.

12. The method of claim 11, wherein said method for acquiring the secondary structure further comprises a step of predicting the bases in said nucleic acid molecule that are capable of forming a stem structure.

13. The method of claim 11, wherein the step of searching a motif sequence is a step in which, when the single-stranded region that accords with any one of a plurality of candidates for the motif sequence is detected, an evaluated value of the nucleotide sequence corresponding to the single-stranded region is added as a score to the candidate for the motif sequence that accords with the single-stranded region, and a candidate for the motif sequence having the largest score is assessed as the motif sequence.

14. The method of claim 11, wherein the step of acquiring the general structure is a step of acquiring a general structure of the nucleotide sequence corresponding to bases having in the center the single-stranded region and the stem structure positioned at both ends of the single-stranded region, from the secondary structure of the nucleotide sequence of the nucleic acid molecule including the single-stranded region that accords with the motif sequence.

15. The method of claim 11, wherein the step of acquiring the general structure is a step of acquiring a general structure of the nucleotide sequence corresponding to bases having in the center the motif sequence and the stem structure positioned at both ends of the single-stranded region, from the secondary structure of the nucleotide sequence of the nucleic acid molecule including the single-stranded region that accords with the motif sequence.

16. The method of claim 11, wherein the evaluated value is a value defined based on a binding constant between the target substance and the nucleic acid molecule.

17. The method of claim 11, further comprising synthesizing an aptamer molecule with the prepared aptamer sequence.

18. The method of claim 17, wherein said aptamer is synthesized by chemical synthesis.

19. The apparatus of claim 10, wherein said one or more programs further comprise commands for predicting the bases in said nucleic acid molecule that are capable of forming a stem structure.

20. The apparatus of claim 10, wherein, when the single-stranded region that accords with any one of a plurality of candidates for the motif sequence is detected, an evaluated value of the nucleotide sequence corresponding to the single-stranded region is added as a score to the candidate for the motif sequence that accords with the single-stranded region, and a candidate for the motif sequence having the largest score is assessed as the motif sequence.

21. The apparatus of claim 10, wherein said acquiring is the acquiring of a general structure of the nucleotide sequence corresponding to bases having in the center the single-stranded region and the stem structure positioned at both ends of the single-stranded region, from the secondary structure of the nucleotide sequence of the nucleic acid molecule including the single-stranded region that accords with the motif sequence.

22. The apparatus of claim 10, wherein said acquiring is the acquiring of a general structure of the nucleotide sequence corresponding to bases having in the center the motif sequence and the stem structure positioned at both ends of the single-stranded region, from the secondary structure of the nucleotide sequence of the nucleic acid molecule including the single-stranded region that accords with the motif sequence.

23. A non-transitory, computer-readable storage medium, storing a program for preparing an optimized aptamer sequence, wherein said program screens nucleic acid sequences by identifying a region within a nucleic acid molecule that binds to a target substance, and wherein said program executes the steps of:
(1) extracting data of a single-stranded region, by excluding bases capable of forming a stem structure from the sequence of the nucleic acid molecule;
(2) searching a motif sequence from the single-stranded region, by weighing the appearance frequency of a specific sequence in the extracted data with an evaluated value of the affinity of the nucleic acid molecule for the target substance; and
(3) preparing and outputting an aptamer sequence that contains the region binding to the target substance, but which lacks one or more corresponding nucleotides that are present in the nucleic acid molecule and which are unnecessary for binding to the target substance.

24. A non-transitory, computer-readable storage medium, storing a program for preparing an optimized aptamer sequence, wherein said program screens nucleic acid sequences by acquiring a secondary structure of a nucleic acid molecule that contains a region that binds to a target substance, and wherein said program executes the steps of:
(1) extracting data of a single-stranded region, by excluding bases capable of forming a stem structure from the sequence of the nucleic acid molecule;
(2) searching a motif sequence from the single-stranded region, by weighing the appearance frequency of a specific sequence in the extracted data with an evaluated value of the affinity of the nucleic acid molecule for the target substance;
(3) acquiring a general structure from a secondary structure of the nucleic acid molecule, based on the single-stranded region that accords with the motif sequence and based on bases forming the stem structure positioned at both ends of the single-stranded region; and (4) preparing and outputting an aptamer sequence that contains the region binding to the target substance, but which lacks one or more corresponding nucleotides that are present in the nucleic acid molecule and which are unnecessary for binding to the target substance.

* * * * *

SEQUENCE LISTING

<160> NUMBER OF SEQ ID NOS: 8

<210> SEQ ID NO 1
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 1
aaaacgcgaa aacgcgaauu                                               20

<210> SEQ ID NO 2
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 2
aaaagcgcag aagcgcaauu                                               20

<210> SEQ ID NO 3
<211> LENGTH: 4
<212> TYPE: RNA
<213> ORGANISM: Artificial Sequence
<220> FEATURE:
<223> OTHER INFORMATION: Synthetic oligonucleotide

<400> SEQUENCE: 3 aaaa                                                                 4

<210> SEQ ID NO 4
<211> LENGTH: 4
<212> TYPE: RNA
<213> ORGANISM: Artificial Sequence
<220> FEATURE:
<223> OTHER INFORMATION: Synthetic oligonucleotide

<400> SEQUENCE: 4 agaa                                                                 4

<210> SEQ ID NO 5
<211> LENGTH: 4
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u

<400> SEQUENCE: 5 anaa                                                                 4

<210> SEQ ID NO 6
<211> LENGTH: 12
<212> TYPE: RNA
<213> ORGANISM: Artificial Sequence
<220> FEATURE:
<223> OTHER INFORMATION: Synthetic oligonucleotide

<400> SEQUENCE: 6
cgcgaaaacg cg                                                       12

<210> SEQ ID NO 7
<211> LENGTH: 74
<212> TYPE: RNA
<213> ORGANISM: Artificial Sequence
<220> FEATURE:
<223> OTHER INFORMATION: Synthetic oligonucleotide

<400> SEQUENCE: 7
gggagaauuc cgaccagaag cgcaagccgg cccuuggaag gcuagucggu ccuuccucu    60

```
cuccuccuuc uucu                                                              74

<210> SEQ ID NO 8
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 8
gggaccagaa gcgcaagccg gcccuuggaa ggcuaguccc                                  40
```